(12) United States Patent
Dauner et al.

(10) Patent No.: US 7,585,617 B2
(45) Date of Patent: Sep. 8, 2009

(54) METHOD AND DEVICE FOR THERMAL CONDITIONING OF A CELL

(75) Inventors: Michael Dauner, Nehren (DE); Jochen Schaub, Stuttgart (DE)

(73) Assignee: Insilico Biotechnology GmbH, Stuttgart (DE)

( * ) Notice: Subject to any disclaimer, the term of this patent is extended or adjusted under 35 U.S.C. 154(b) by 0 days.

(21) Appl. No.: 10/598,377

(22) PCT Filed: Feb. 26, 2005

(86) PCT No.: PCT/EP2005/002065

§ 371 (c)(1),
(2), (4) Date: Jun. 22, 2007

(87) PCT Pub. No.: WO2005/083054

PCT Pub. Date: Sep. 9, 2005

(65) Prior Publication Data

US 2007/0298484 A1      Dec. 27, 2007

(30) Foreign Application Priority Data

Feb. 27, 2004    (DE) .................. 10 2004 010 828

(51) Int. Cl.
*C12Q 3/00*        (2006.01)
*C12M 1/00*        (2006.01)
*C12N 1/06*        (2006.01)
*G01N 33/48*       (2006.01)

(52) U.S. Cl. .............................. 435/3; 435/4; 435/91.1; 435/259; 435/270; 435/283.1; 435/306.1; 436/63; 536/23.1; 536/25.4

(58) Field of Classification Search .................. None
See application file for complete search history.

(56) References Cited

U.S. PATENT DOCUMENTS 5,837,452 A    11/1998  Clark et al.
6,197,553 B1    3/2001  Lee et al.

FOREIGN PATENT DOCUMENTS

| DE | 1 814 084   | 6/1970 |
| EP | 0 217 622 A2 | 4/1987 |
| EP | 0 722 075 A1 | 7/1996 |

*Primary Examiner*—Herbert J. Lilling
(74) *Attorney, Agent, or Firm*—Gail C. Silver; Borden Ladner Gervais LLP

(57) ABSTRACT

The invention relates to methods and agents for thermal conditioning of a biological cell, methods and uses of said agents for releasing and insulating ingredients outside the biological cell, and for quantitatively and qualitatively detecting the released ingredient and to a method for sampling biological cells which consists in carrying out in one step the sampling said biological cells in a culture medium and in releasing cellular ingredients during said sampling. Sampling devices are also disclosed.

16 Claims, 10 Drawing Sheets

METHOD AND DEVICE FOR THERMAL CONDITIONING OF A CELL

The invention relates to a method and means of thermal conditioning of a biological cell, and methods for and applications of said means for liberating and isolating component materials contained in a biological cell and for qualitative detection and quantitative determination of the said liberated materials.

The invention also relates to a method of sampling which accomplishes the transfer of a sample of biological cells from a culture medium, in a single step, and accomplishes liberation of materials contained in said cells, in the course of the transfer; and apparatuses for carrying out the sampling.

Vital biological cells maintain their cell structure under physiological growth conditions. The presence of the cytoplasmic membrane, and membranes of various cell compartments, are responsible for the fact that the only materials released to the cell surroundings are metabolic end products or messenger substances; generally, no significant amounts of cell component materials, particularly metabolites, are released to the cell surroundings. A "metabolite" is understood to mean any essentially low molecular weight substance produced in biological metabolism. It is to be distinguished from so-called biopolymers such as proteins, DNA molecules, mRNA molecules, etc.; however, the precursors and prior stage products, decomposition products, and cleavage products, of biopolymers may be deemed "metabolites".

In order to recover cell component materials, particularly metabolites, from biological cells, certain methods have been employed in the state of the art for a long time without being changed. These methods all have significant drawbacks.

In the established methods, as a rule, the cellular integrity is interfered with. Examples are liberation of metabolites with the use of: ultrasound, mechanical cell degradation methods (e.g. rotary ball mills, with or without impellers), and the method, known for many years, of application of boiling water or supercritical solutions, e.g. in autoclaves. It is known that, with extended heating in boiling water, biological cells will liberate macromolecules, such as plasmid DNA, into a culture solution (Gerhardt, P., Murrac, R. G. E., Wood, W. A., and Krieg, N. R., 1994, "Methods for general and molecular bacteriology", pub. American Society for Microbiology, Washington, D.C.; Sambrook, J., Fritsch, E. F., and Manlatis, T., 1989, Molecular cloning: A laboratory manual", 2nd Ed., pub. Cold Spring Harbor).

Other known methods of liberating metabolites, e.g. the use of chemical solvents, acids, alkalis, and nonpolar solvents, modify the composition of the sample suspensions in a manner such as to render unfeasible the subsequent use of certain detection methods, such as enzymatic assays to determine metabolite concentrations. Also, chemical solvents cause precipitation reactions and/or chemical reactions of the metabolites, leading to incorrect results of various measurements and analytic techniques. Accordingly, one seeks methods of cell degradation wherewith and whereby the liberated component materials, in particular metabolites, can be obtained essentially unchanged. The application of chemical reagents, and freeze-dry cycles, are additional known methods of cell degradation (or lysis).

These methods place thermal, chemical, and/or mechanical stresses on the biological cells, which cells then lose their cell structure or cellular structural integrity, which is to say they indeed undergo lysis. The cell wall and cytoplasmic membrane are severely damaged, and the component materials in the cell are released. In the process, cellular debris is formed, e.g. in the form of micelles, naked DNA, and protein complexes.

After such processes, undesirable materials, namely cell debris, naked DNA, and protein complexes, are present in the cell suspension along with the desired liberated cell component materials, after the cell lysis. The presence of the undesirable materials usually interferes with the detection and analysis of the desired cell components, particularly metabolites. Therefore after cell lysis one must employ purification steps, such as chromatographic and/or electrophoretic separation, in order to obtain the desired component materials, particularly metabolites, in the desired purity. Such separations are necessary preliminaries to analytical methods (detection or analysis) (whether or not combined with other specific preparations for the detection or analysis), e.g. analytical methods for the desired metabolites such as chromatographic, enzymatic, and/or mass spectrographic methods. Accordingly, there is a need in the art for an improved method of recovery of desired cell components, particularly metabolites, from biological cells, which method is easy to carry out and which minimizes contamination of the liberated cell components with interfering materials such as cellular debris, naked DNA, and protein complexes.

Sample-taking methods, particularly for transferring samples of biological cells from culture vessels (e.g. bioreactors) into a sampling vessel, are known. Such methods are particularly important in the study of physiological parameters of biological cells, and in analyses auxiliary to processes in biotechnology and biological process engineering. In such sample-taking methods, the following parameters are sought:

(1) Maximally rapid transfer of cell suspensions from a cell culture system to a sample-taking vessel, in order to enable frequent sampling (hereinafter, "transfer");

(2) Prompt quenching of the metabolism, so that the desired metabolites are not further transformed via enzymatic reactions (hereinafter, "quenching");

(3) Maximally complete liberation of the metabolites from the cells, through use of various degradation techniques (hereinafter, "degradation");

(4) Separation of the metabolites contained in the sample solution, viz. separation from cellular debris and non-lyzed cells (hereinafter, "separation"); and (5) (Optionally, for quantitative biology,) additional constraints, such as the need to take into account the stability of the metabolites in the various steps, and the degree of liberation of the metabolites (which may require taking into account their adsorption to components of the cell suspension and to supplemental materials) (hereinafter, "quantifiability").

A rapid sample-taking method was developed by Theobald et al. (1993, "In vivo analysis of glucose-induced fast changes in yeast adenine nucleotide pool applying a rapid sampling technique", Anal. Biochem., 214, 31-37). This sampling method employs a thin capillary (inner diameter 0.7 mm) comprised of special alloy steel, and a ball valve. An important design criterion was minimization of the dead volume (here 200 microliter), because the sampling was accomplished by discrete opening and closing of the ball valve. The dead volume of 200 microliter is relatively small, for a total sample volume of 5 mL per sampling. This sampling method does not include means of quenching the metabolism nor means of extraction of the desired metabolites. The discrete openings and closings of the ball valve do not envision any means of automation. The means of conveyance of the cell suspension is via sampling tubes to which a vacuum is applied (by vacuum pump, 0.003 mbar). Because the sampling is non-automated, the sampling frequency is only c. 1 in 5 seconds (0.2 per second).

Refinements are provided in the sampling method of Lange et al. (2001, "Improved rapid sampling for in vivo kinetics of intercellular metabolites in *Saccharomyces cerevisiae*", Biotechnol. Bioeng., 7, 406-415). The dead volume is reduced to 50 microliter per sampling, by the use of a bypass line, and by individual control of separate respective valves for the sampling line and the bypass line. By rapid valve actuation to switch between these two lines, one can prevent samples from being withdrawn from the dead space. Also, the losses of sample are minimized. The geometrical dimensions (inner diameter of the capillaries 1.0 mm, length 80 mm) are similar to those of the sampling according to Theobald et al. The means of conveyance of the cell suspension again comprise discrete means, with the use of a vacuum from a vacuum pump, whereby the samples are transferred to pre-sealed test tubes. The sampling frequency is also low, being c. 1.5/sec. for the fluid conveyance alone. Moreover, this sampling frequency number does not take into account the time for establishing the vacuum (c. 1 sec) and the time to manually change the individual test tube.

In the known sampling devices, the quenching of the metabolism and the extraction of the desired metabolites occurs in units which are mutually separate (from the standpoint of engineering design) and thereby are timewise separate and non-integrated during sampling and through the sampling system. Accordingly, quenching and metabolite liberation are process steps which are partially separate but which are also partially combined in one step (in the sense that chemical actions take place in a unitary second phase (e.g., acids, bases, liquid nitrogen, or substantially cooled methanol)).

German Patent Application DE 4407439 A1 discloses a "Method and apparatus for serial sample-taking of biological samples", wherein a sample is withdrawn semi-continuously into a helical polypropylene tube (inner diameter 8 mm, length 100 mm, helix diameter 0.5 m) until the tube is filled with the cell suspension and parallel-dosed perchloric acid (35% wt./vol., at −25° C.). The perchloric acid causes immediate inactivation of the metabolism, with simultaneous disruption of the cell structure and release of the metabolites. When the helical tube is filled it is frozen to −80° C. This can then be thawed in separate pieces, wherewith the position of a sample segment in the tube may be correlated with, e.g., a given time point in the changes of the culture conditions (which culture conditions may include, e.g., dynamic stimulation (such as pulsed increases in the glucose concentration, in a glucose-limited culture)).

A means of continuous sampling is described in DE 19705289 A1. The sampling is continuous, but there is no provision for simultaneous quenching or for liberation of metabolites.

Accordingly, the basic requirements applicable to a method which provides quenching, degradation, and separation are:

(i) Maximally rapid quenching of the metabolism, i.e. complete and irreversible inactivation and denaturing of the enzymes, and the immediate separation-out of the enzymes;

(ii) Reproducible (and thus generally maximally complete) disruption of the cell structure, and/or permeabilization of the cell membrane, to achieve complete liberation of the metabolites from the cells;

(iii) Easy separation of metabolites, cell fragments, and cells;

(iv) Preservation of the structural integrity (chemical structure) of the desired metabolites in the course of (i)-(iii), sufficiently to allow clear identification and analysis. Further, for the sake of quantitative analysis, a reproducible liberation is necessary in the various steps, and there must be no interfering phenomena such as non-reproducible adsorption of metabolites onto auxiliary agents.

Typically, there will be two process stages for carrying out quenching, degradation, and separation. In one stage, quenching and degradation will be carried out, and in the other stage, filtration and centrifugation will be carried out (to achieve the separation). The metabolism may be quenched by chemical reagents or by imposing a temperature gradient.

According to Theobald et al. (loc. cit.), perchloric acid (35% wt./vol., at −25° C.) is charged into sealed test tubes under vacuum; and thus temperatures below the freezing point of aqueous solutions are utilized to quench the metabolism, with superimposed extraction by cooled perchloric acid. Further, three cycles of freeze drying are carried out (the ice crystallization renders the cell walls permeable). Prior to the analysis, the samples must be neutralized, and the $KClO_4$ precipitate must be removed in a filtration step.

According to Lange et al. (loc. ct), temperatures below the freezing point of aqueous solutions are also used, with addition of 5 ml methanol (at −40° C.) as a quenching agent. The metabolite extraction is accomplished with boiling ethanol, applied to the cell pellet obtained by centrifugation.

According to DE 19705289 A1, a methanol mixture at −50° C. is employed as a quenching liquid, followed by centrifugation (−20° C.), re-suspension of the pellet with perchloric acid, a freeze drying cycle (−80° C.) for extraction of the metabolites, neutralization of the solution, and re-centrifugation to remove the precipitates.

Further, liquid nitrogen may be used in connection with freeze drying cycles, for quenching and/or extraction; and boiling water may be employed instead of boiling ethanol (Bhattacharya, Fuhrman, Ingram, Nickerson, and Conway, 1995, "Single-run separation and detection of multiple metabolic intermediaries by anion-exchange high performance liquid chromatography and application to cell pool extracts prepared from *Escherichia coli*" Anal. Biochem., 232, 98-106).

Apparatuses are known which are structured for operation as heat exchangers, particularly for use as sterilization units for thermal treatment of small-volume flows. EP 0722075 A1 discloses a small sterilization unit for continuous operation on the laboratory scale or small pilot scale. The gas stream is symmetrically divided to send equal volumes of flow to a plurality of tubes of equal length, via elaborately configured distributional cover elements. For sterilization, brief heating at c. 140° C. is proposed.

DE 2345243 A1 discloses a steam-heated heat exchanger. Characteristically, optimized heat transfer is attained by helical flow guides and by geometric variation of the flow cross section.

WO 92/16807 discloses an apparatus which also employs helical tubes, to increase the surface and to optimize the flow parameters, and which has liquid injectors as a feature. These serve to increase creation of vortices and turbulent flow, thereby improving the heat transfer.

The brief heating of biological samples by microwaves is also known, e.g. from EP 012762 A1, which includes descriptions of both the method of microwave sterilization and the apparatus required therefor.

None of the abovementioned known apparatuses is a cell conditioning apparatus which is specifically usable for liberation and isolation of desired cell components, particularly metabolites, from biological cells.

With the state of the art as the point of departure, the underlying technical problem of the present invention was to devise a method and means of thermal conditioning of a cell, which method and which means generally enable improved liberation and isolation of desired cell component materials from biological cells, and which in particular enable improved qualitative detection and quantitative determination of the liberated component materials.

This technical problem was solved by a method of thermal conditioning of a biological cell wherein the cell is cultured at a culture temperature $T_M$, in a culture medium, after which it is conditioned for a conditioning time $t_h$ at a conditioning temperature $T_K$, which method is characterized in that the "thermal equivalent", WE, determined from $T_M$, $T_K$, and $t_h$ according to the formula:

$$WE = t_h \cdot (T_K - T_M),$$

is in the range 70-300° K.·sec.

This means that according to the invention the parameters $T_M$, $T_K$, and $t_h$ are chosen such that the "thermal equivalent" is in the range 70-300° K.·sec.

An essential aspect of the present invention is that the cells are treated for complete liberation of metabolites without interference with the structural integrity of the cells. "Structural integrity of the cells" is understood to mean that the cell envelope (cell wall and membranes) remains in one piece, and no fragments are formed from it. Accordingly, no significant formation of cell fragments occurs ("cell fragments" are subcellular particles, such as micelles from the cytoplasmic membrane, naked DNA fragments, mRNA, and protein complexes). E.g., if one views *E. coli* cells which are completely intact and *E. coli* cells "with structural integrity" in a simple optical transmission microscope at overall magnification 500×(ocular×tube×objective=10×1.25×40), one cannot distinguish them by their sizes.

The inventors have discovered, surprisingly, that liberation of desired cell components, particularly metabolites, is achieved by the inventive thermal conditioning in a narrow temperature range prescribed via the "thermal equivalent", WE, and the precisely prescribed time duration; while at the same time, particularly advantageously, the cell structure of the thermally conditioned biological cells is maintained. Essentially, following the inventive thermal conditioning, one has: the liberated desired cell components, particularly metabolites; and "emptied" cell envelopes with intact structure preserved.

The presence of cellular debris and other undesirable and interfering component materials is reduced, and, by an appropriate choice of parameters and depending on the given application, may indeed be completely eliminated. It is particularly advantageous that a simple and efficient separation of these cell envelopes with intact structure from the metabolites is possible, by means of simple filtration and/or centrifugation. In this way, particularly advantageously, the intracellular metabolites can be subjected to qualitative and/or quantitative analysis, immediately after the conditioning, without intervention of additional costly or time-consuming intermediate steps.

The areas of applicability of the inventive technical teaching are, in particular, methods and apparatuses for determining intracellular metabolite concentrations in various cell systems, such as those of microorganisms, fungi, or cell cultures of animal, human, or plant cells, in culture systems such as bioreactors, shaking flasks, test tubes, or microtitration plates.

The invention may be used for the study of steady or non-steady physiological states of biological cells. The invention enables very rapid quenching of the cell metabolism. The selective liberation of metabolites by thermally conditioned cells according to the invention enables easy sample preparation and purification for analysis.

Thus, e.g., in carrying out enzymatic assays and photometric determination of light scattering and light absorption, the invention enables avoidance of turbidity in the sample solution, which turbidity is unavoidable in known liberation methods because cellular debris and other interfering component materials enter into suspension in the medium when one carries out complete degradation of the cell structure with subsequent separation by filtration. When chromatographic methods such as HPLC analysis are employed, blocking of, e.g., the HPLC column, by large pieces of cellular debris is avoided.

According to a preferred embodiment of the inventive method, the conditioning temperature $T_K$ is in the range 65-105° C., preferably 80-95° C. In particular, the advantageous effects are achieved at temperatures in the range 80-95° C.; however, advantageous effects are possible at higher and lower temperatures than these, depending on the given application and the purpose at hand. The conditioning temperature which ought to be used in a given case can be easily determined by a person skilled in the art, by application of his accumulated knowledge and skill. In a preferred variant, the conditioning temperature $T_K$ is always below the boiling point of the culture medium. According to the invention it is preferable to always avoid boiling the culture medium containing the biological cells; this is a substantial distinction from the state of the art.

According to a preferred embodiment of the inventive method, the conditioning time $t_h$ is in the range 0.5-600 sec, preferably 1-180 sec. The advantageous effects are particularly achieved at conditioning times of 0.5-600 sec; however, advantageous effects are possible at longer or shorter times than these, depending on the given application and the purpose at hand. The conditioning time which ought to be used in a given case can be easily determined by a person skilled in the art, by application of his accumulated knowledge and skill.

According to a preferred embodiment of the inventive method, the culturing temperature $T_M$ is in the range 26-42° C., preferably 30-38° C. The culturing temperature which ought to be used in a given case can be easily determined by a person skilled in the art, by application of his accumulated knowledge and skill.

According to a particularly preferred embodiment of the inventive method, the value of the "thermal equivalent", WE, calculated according to the invention from the culturing temperature $T_M$, the conditioning temperature $T_K$, and the conditioning time $t_h$, is in the range 90-150° K.·sec.

According to a preferred variant of the inventive method, used for thermal conditioning of a biological cell which is a gram-negative prokaryote, the optimal "thermal equivalent", WE, for this organism is 110±20° C. An example of a gram-negative prokaryote is the bacterium *Escherichia coli* (*E. coli*).

According to another preferred variant of the inventive method, used for thermal conditioning of a biological cell which is a eukaryote, the optimal "thermal equivalent", WE, for this organism is 110±20° C. An example of a eukaryote is the yeast *Saccharomyces cerevisiae* (*S. cerevisiae*).

According to yet another preferred variant of the inventive method, used for thermal conditioning of a biological cell which is a gram-positive prokaryote, the optimal "thermal equivalent", WE, for this organism is 130±20° C. An example of a gram-positive prokaryote is the bacterium *Bacillus subtilis* (*B. subtilis*).

According to still another preferred variant of the inventive method, the culture medium is a liquid, and in the thermal conditioning the medium containing the cells is flowed through a capillary, wherewith during the conditioning, carried out for a conditioning time $t_h$, the cells are disposed in a segment of the capillary at the conditioning temperature $T_K$. According to the invention, preferably the corresponding value of the "thermal equivalent", WE, is transferred and the biological cells are thermally conditioned according to the invention. In a preferred variant, the volumetric flow rate in the temperature-controlled segment of the capillary is preferably in the range 0.5-12 mL/sec, particularly preferably 2.5-8.0 mL/sec.

According to yet another preferred variant of the inventive method, the step of thermal conditioning is carried out with the transfer of the culture medium containing the biological cells from a culturing vessel, particularly a bioreactor, to a receiving vessel, particularly a sample collection vessel. In this process, advantageously there are carried out: a rapid transfer, of, e.g., a cell suspension, from a cell culturing system into a sample-taking vessel; prompt quenching of the metabolism in the cell, and simultaneously liberation of the metabolites from the cells; whereby the thermal conditioning of the biological cells is achieved in a single process step connected with the sample transfer. Particularly advantageously, the invention enables, immediately successive to this sample transfer, qualitative and/or quantitative analyses of the liberated metabolites (or the particular metabolites of interest), and the isolation and recovery of said metabolites. In particular, after the thermal conditioning in connection with the sample transfer, and after simple filtration or centrifugation, the metabolite is made available in an advantageously high purity. Complex and time-consuming purification steps are rendered unnecessary; thus, it is possible to achieve timely continuous analysis of metabolites and/or recovery of metabolites, and/or a high sampling frequency. Also, a high sample throughput can be achieved, and uniform quality, which quality depends on a small number of factors.

The present invention also relates to recovery, and qualitative and/or quantitative analysis (or determination) of component materials contained in biological cells, in particular at least one intracellular metabolite. This metabolite is preferably selected from the group of metabolites comprised of amino acids and their derivatives, amines and their derivatives, carboxylic acids, alcohols, aldehydes, ketones, phosphate esters other than nucleic acids, nucleic acids and congeners, sugars and congeners, lipids, steroids, fatty acids, vitamins, coenzymes, and inorganic ions.

The metabolites recovered by means of the hereinbelow described inventive methods, and detected qualitatively and/or determined quantitatively, are in particular:

| Metabolite class: | Specific metabolites: |
|---|---|
| Amino acids, amines, and their derivatives: | alanine, glutamate. |
| Carboxylic acids: | pyruvate, citrate, isocitrate, oxoglutarate, oxaloacetate, malate, fumarate, succinate, phosphoglycerate, phospho-enol-pyruvate. |
| Alcohols: | ethanol. |
| Phosphate esters, other than nucleic acids: | ppGpp, NAD, NADP, NADH, NADPH. |
| Nucleic acids, and congeners: | adenosine monophosphate, guanosine triphosphate, uridine diphosphate, cAMP (adenosine-3',5'-monophosphate). |
| Sugars, and congeners: | glucose phosphate, fructose phosphate, fructose bisphosphate, phosphogluconate, ribose phosphate and ribulose phosphate, erythrose phosphate, sedoheptulose phosphate, dihydroxyacetone phosphate. |
| Lipids, steroids, and fatty acids: | acetyl-CoA. |
| Vitamins and coenzymes: | riboflavin. |
| Inorganic ions: | phosphate. |

Other metabolites which can be isolated and/or recovered, and can be detected qualitatively and/or determined quantitatively, according to the invention, are: aminobutanoate, acetoacetate, acetoacetyl-CoA, acetaldehyde, acetyl-L-carnitine, acetyl-CoA, acetate, acetyladenylate, acetohydroxybutanoate, S-acetyldihydrolipoamides, N-acetyl glutamate, N-acetyl glutamate phosphate, N-acetyl glutamate semialdehyde, O-acetyl homoserine, 2-acetolactate, N(2)-acetylornithine, acetylphosphates, N-acetyl glucosamine, N-acetyl glucosamine phosphate, acyl glycerin, 1-acyl-sn-glycerin-3-phosphate, 1-acylglycerophosphocholine, 1-acyl-sn-glycerin-3-phosphoethanolamine, N-acetyl mannosamine, N-acetyl mannosamine phosphate, 2-amino-3-carboxymuconate semialdehyde, N-acetyl neuraminate, N-acetyl-neuraminate-9-phosphate, adenine, adenosine, adenylosuccinate, adenylyl sulfate, adenosine diphosphate, ADP-ribose, ADP-ribose phosphate, 1-(5'-phosphoribosyl)-5-formamido-4-imidazole carboxamide, AICAR, aminoimidazole ribotide, ketoglutarate, ketovaline, alanine, aminoacetoacetate, aminoacetone, aminoadipate adenylate, aminoadipate semialdehyde, aminobenzoate, aminolevulinate, adenosine monophosphate, 2-aminomuconate, 2-aminomuconate semialdehyde, arginine, (N-omega-L-arginino)succinate, arogenate, S-adenosyl methionineamine, asparagine, aspartate, aspartyl phosphate, aspartate semialdehyde, adenosine triphosphate, betaine, betaine aldehyde, CMP N-acetyl neuraminate, cAMP, carnitine, N-carbamoyl L-aspartate, carbamoyl phosphate, cardiolipine, cytidine diphosphate, CDP-choline, CDP-diacylglycerin, CDP-ethanolamine, ceramides, cGMP, cholesterol, cholesta-7,24-diene-3-betaol, choline, choline phosphate, chorismate, 3-carboxy-1-hydroxypropyl-ThPP, aconitate, methylaconitate, citrate, citrulline, cytidine monophosphate, coenzyme A, coenzyme Q, creatine, phosphocreatine, crotonoyl-CoA, cytidine triphosphate, cysteine, cystathione, cystine, cytidine, deoxyadenosine, deoxyadenosine diphosphate, deamino-NAD, deoxyadenosine monophosphate, deoxyadenosine triphosphate, deoxycytidine diphosphate, deoxycytidine monophosphate, deoxycytidine triphosphate, cytidine, demethyllanosterol, 4,4-dimethyl-5-cholesta-8,14,24-triene-3-betaol, deoxyguanosine triphosphate, deoxyguanosine monophosphate, deoxyguanosine triphosphate, deoxyguanosine, dihydroxyacetone phosphate, dehydrocholesterol, dihydrofolate, dihydrolipoamide, dihydroneopterin, (S)-dihydroorotate, dihydropteroate, dihydrobiopterin, amino-4-hydroxy-6-hydroxymethyl-dihydropteridin, 2-amino-7,8-dihydro-4-hydroxy-6-(diphosphooxymethyl)pteridine, 3-dehydroquinate, dehydrosphinganine, diacylglycerin, diacylglycerin phosphate, dimethylglycine, deoxyinosine, dimethylallyl diphosphate, dimethylglycine, N-acetyl-D-glucosaminyl diphosphodolichol, N,N'-chitobiosyl diphosphodolichol, dolichol, dolichyl phosphate, dolichyl diphosphate, dehydropantoate, dephospho-CoA, 2-deoxy-D-ribose phosphate, 3-dehydroshikimate, deoxythymidine diphosphate, deoxythymidine monophosphate, deoxythymidine triphosphate, deoxyuridine diphosphate, deoxyuridine monophosphate, deoxyuridine, deoxyuridine triphosphate, erythrose phosphate, ethanolamine, ethanol, fructose phosphate, fructose bisphosphate. FAD, farnesyl diphosphate, 2-(formamido)-N1-(5'-phosphoribosyl)acetamidine, 5'-phosphoribosyl-N-formylglycinamide, fumaryl acetoacetate, formiminotetrahydrofolate, formyl kynurenine, Fosäure, formate, formaldehyde, formiminoglutamate, fructose, formyltetrahydrofolate, fumarate, glucose phosphate, glycerate-2-phosphate, glycerate-3-phosphate, galactose, alpha-D-galactose-1-phosphate, D-glyceraldehyde, glyceraldehyde-3-phosphate, 5-phosphoribosyl glycinamide, guanosine diphosphate, GDP-dehydrodeoxymannose, GDP-fucose, GDP-mannose, geranyl diphosphate, gluconolactone phosphate, glyceraldehyde, glucosamine, glucosamine phosphate, glucose, glutamine, glycolate, glycerophosphocholine, glycerophosphoethanolamine, gluconate, phosphogluconate, glutamate, glutamate phosphate, glutamate semialdehyde, glutamyl L-cysteine, glutathione, glutaryl-CoA, glycine, glycerin, glycerin phosphate, glycolaldehyde, glycerone, glyoxylate, glycerate, guanosine monophosphate, guanosine triphosphate, guanine, guanosine, guanidinoacetate, hydrogen ions, hydrogen peroxide, hydroxyanthranilate, hydroxybutane tricarboxylate, homocitrate, hydrogen carbonate, homocysteine, hydroxykynurenine, hydroxyproline, hydroxypyruvate, histidine, homoisocitrate, hydroxmethylglutaryl-CoA, homogentisate, 3-(4-hydroxyphenyl)pyruvate, sulfide, homoserine, O-phosphohomoserine, 2-(alpha-hydroxyethyl)thiamine diphosphate, hypoxanthine, hydroxybutanoyl-CoA, hydroxyisobutyryl-CoA, hydroxyisobutyrate, (2S,3S)-3-hydroxy-2-methylbutanoyl-CoA, 4-hydroxyphenylpyruvate, isoleucine, 4-imidazolone-5-propanoate, D-erythro-1-(imidazol-4-yl) glycerin-3-phosphate, inosine monophosphate, indole, indoleglycerin phosphate, inosine, isobutyryl-CoA, isocitrate, isopropyl malate, isopentenyl diphosphate, potassium ion, kynurenine, lactose, lactate, lactaldehyde, lanosterol, lathosterol, leucine, lactoylglutathione, lipoamide, linolenic acid, linoleic acid, lysine, malate, malonyl-CoA, mannose, mannose phosphate, methenyltetrahydrofolate, methionine, methylacetoacetyl-CoA, methylbutenoyl-CoA, methyloxopentanoate, methacrylyl-CoA, methylthioadenosine, methylglyoxal, methylglutaconyl-CoA, methyl tetrahydrofolate, methanethiol, methylmalonate semialdehyde, methylenetetrahydrofolate, mevalonate, phosphomevalonate, diphosphomevalonate, inositol, maleyl acetoacetate, mercaptopyruvate, methyltetrahydropteroyl triglutamate, sodium ion, NAD, NADH, NAD phosphate, ammonium ion, nicotinate, nicotinamide, nicotinamide diribonucleotide, nicotinate ribonucleotide, oxaloacetate, hydroxide ion, oleic acid, oleoyl-CoA, ornithine, orotate, orotidine phosphate, oxoadipate, methyloxobutanoate, oxobutanoate, oxalosuccinate, orthophosphate, phosphadenylyl sulfate, palmitate, palmitoyl-CoA, palmithionate, pantothenate, pantoate, pantetheine, phosphoenol-pyruvate, phosphoethanolamine, bisphosphoglycerate, phenylalanine, phenylpyruvate, phosphohydroxypyruvate, pyrophosphate, phosphopantothenate, pantetheine phosphate, phosphopantothenoylcysteine, prephenate, phosphoribosyl glycinamide, phosphororibosylamine, proline, propanoate, propanoyl-CoA, phosphoribose-1-diphosphate, phosphoserine, presqualene diphosphate, phosphatidylcholine, phosphatidyl-N-dimethylethanolamine, phosphatidylethanolamine, phosphatidylglycerin, phosphatidylglycerophosphate, phosphatidyl-N-methyl-ethanolamine, 1-phosphatidyl-D-myo-inositol, phosphatidylserine, putrescine, pyrrolinecarboxylate, pyruvate, pyridoxal phosphate, ppGpp, quinolinate, 1-(5-phospho-D-ribosyl)-5-amino-4-imidazolecarboxylate, ribose, ribose phosphate, ribulose phosphate, methyl-3-oxopropanoyl-CoA, thiosulfuric acid ion, adenosylhomocysteine, 1-(5'-phosphoribosyl)-5-amino-4-(N-succinocarboxamide)-imidazole, adenosylmethionine, saccharopine, sorbitol, sedoheptulose-7-phosphate, serine, methyl-3-oxopropanoyl-CoA, sulfite ion, sulfate ion, spermidine, sphingomyelin, sphingenine [lit., "sphinganine"], sphingosine, squalene, squalene epoxide, stearate, stearoyl-CoA, succinate, succinyl-CoA, S-succinyl-dihydrolipoamide, succinylhomoserine, succinate semialdehyde, thiocysteine, tetrahydrofolate, tetrahydrobiopterine, thiamine diphosphate, threonine, thymidine, tetrahydropteroyl triglutamate, threhalose, trehalose phosphate, triacyl glycerin, tryptophan, tyrosine, UDP-N-acetyl-D-glucosamine, UDP-N-acetyl-D-galactosamine, ubiquinol, ubiquinone, uridine diphosphate, UDP-galactose, UDP-glucose, uridine monophosphate, uracil, urea, allophanate, uridine, urocanate, uridine triphosphate, valine, xanthine, xanthosine, xanthosine phosphate, xylulose phosphate, and zymosterol.

Taking into account the preceding, the claimed matter of the present invention includes a method of recovering a component material, particularly at least one metabolite, from a biological cell, which method comprises the following steps:

(a) Culturing of at least one biological cell in a culture medium;

(b) Thermal conditioning of the at least one biological cell according to the inventive method, wherewith or whereby the component material, in particular the at least one metabolite, is liberated from the at least one thermally conditioned cell;

(c) Isolation of the liberated component material, in particular the at least one metabolite, from the culture medium.

Particularly preferably, step (a) of the method is carried out in a culturing vessel, particularly in connection with a liquid culture medium, e.g. in a culture suspension. One skilled in the art can select advantageous culturing conditions for the area of application with which he is concerned, in connection with existing technical teaching or within the ambit of other knowledge which he may possess.

Particularly preferably, step (b) of the method is carried out in connection with sample-taking and transfer of the sample(s) into a receiving vessel, particularly a sampling vessel, e.g. in a sampling device provided for the purpose.

Step (c) of the method may be carried out in a manner which is per se known, using known purification techniques. Particularly preferred, and particularly advantageous according to the present invention, as well as being suitable and adequate, are simple mechanical separation techniques such as filtration, e.g. with a simple sterile filter, preferably having pore size 0.2 micron, or centrifugation. Advantageously, these separation techniques serve to separate-out the cell envelopes (intact) of the thermally conditioned cells. The desired cell components, particularly the at least one metabolite, will be present in the filtrate (or centrifugation supernatant). It should be understood that one skilled in the art may select the separation, purification, and isolation methods, in place of or supplemental to those described herein, as deemed advantageous for the area of application at hand, taking into account available technical teaching and other knowledge which he may possess.

The claimed matter of the present invention also includes a method for quantitative determination of a component material, particularly at least one metabolite, in at least one biological cell, which method includes the following steps:

(a) Culturing of the cells in a culture medium;
(b) Thermal conditioning of the at least one biological cell according to the inventive method, wherewith or whereby the component material, in particular the at least one metabolite, is liberated from the at least one thermally conditioned cell;
(c) Quantitative determination of the liberated component material, in particular the at least one metabolite, in the culture medium.

Particularly preferably, step (a) of the method is carried out in a culturing vessel, particularly in connection with a liquid culture medium, e.g. in a culture suspension. One skilled in the art can select advantageous culturing conditions for the area of application with which he is concerned, in connection with existing technical teaching or within the ambit of other knowledge which he may possess.

Particularly preferably, step (b) of the method is carried out in connection with sample-taking and transfer of the sample(s) into a receiving vessel, particularly a sampling vessel, e.g. in a sampling device provided for the purpose.

Step (c) of the method may be carried out in a manner which is per se known, using known methods of quantitative determination of the metabolites of interest.

The claimed matter of the present invention also includes a method for qualitative detection of a component material, particularly at least one metabolite, in at least one biological cell, which method includes the following steps:
(a) Culturing of the cells in a culture medium;
(b) Thermal conditioning of the at least one biological cell according to the inventive method, wherewith or whereby the component material, in particular the at least one metabolite, is liberated from the at least one thermally conditioned cell;
(c) Qualitative detection of the liberated component material, in particular the at least one metabolite, in the culture medium.

Particularly preferably, step (a) of the method is carried out in a culturing vessel, particularly in connection with a liquid culture medium, e.g. in a culture suspension. One skilled in the art can select advantageous culturing conditions for the area of application with which he is concerned, in connection with existing technical teaching or within the ambit of other knowledge which he may possess.

Particularly preferably, step (b) of the method is carried out in connection with sample-taking and transfer of the sample(s) into a receiving vessel, particularly a sampling vessel, e.g. in a sampling device provided for the purpose.

Step (c) of the method may be carried out in a manner which is per se known, using known methods of qualitative detection of the metabolites of interest.

The present invention also relates to an apparatus for sample taking, particularly for transfer of a sample of biological cells from microbial, particularly fungal or bacterial, cultures or mixed cultures, and cell cultures of vegetable, animal, or human cells. These cells may be cultured in a culture system such as a bioreactor, shaking flask, test tube, or microtitration plate. The invention provides for a sample to be taken from the culturing system and transferred to at least one receiving vessel. It is preferable according to the invention that the thermal conditioning of the biological cells in the sample take place during this process.

The claimed matter of the invention also includes a cell conditioning device as a component of such a sample-taking apparatus. The inventive cell conditioning device serves for thermal conditioning of at least one biological cell which cell is preferably suspended in a liquid culture medium. The inventive cell conditioning device comprises at least one capillary disposed adjacent to a heat source, through which capillary a liquid culture medium is flowed, wherewith preferably the described cell sample suspended in the culture medium is transferred through said capillary. According to the invention the device is characterized in that the capillary has an internal diameter of 0.5-4.5 mm, preferably 1.0-3.0 mm, and the capillary is in contact with the heat source along a temperature-controlled capillary segment of 50-1550 cm, preferably 90-420 cm.

Preferably the cell conditioning device serves for carrying out the described inventive method of thermal conditioning. As described, the inventive method is particularly distinguished in that certain process parameters are maintained which have surprising advantageous technical effects.

To perform sample-taking along with thermal conditioning, a cell suspension is withdrawn from the culturing system and is transferred into a sample receiving vessel, via a first segment of the capillary which segment is designed as a short transferring segment, and via a second capillary segment which adjoins the first segment and which is realized as a temperature-controlled segment.

It was found, surprisingly, that these process parameters can be maintained using the inventive cell conditioning device, if certain geometric constraints are observed in the dimensioning of the capillary of the cell conditioning device. Table 1 shows the relationship between the interior diameter of the helical tube and the length of the temperature-controlled capillary for maximum volumetric flow rates of 2.5 and 8 mL/sec, and for maximum "turnover" times of the intracellular metabolite (e.g. ATP) of tau=0.1 and 2.7 sec. The values obtained may be extended for any intermediate values of the volumetric flow rate ($\dot{V}$) for example 2.5 mL/s<$\dot{V}$<8 mL/s, and of the "turnover" time, tau ($\tau$) (for example 0.1<$\tau$<2.7 sec).

TABLE 1

| Volumetric flow rate (mL/sec) | "Turnover" time tau ($\tau$) (sec) | "Thermal equivalents" WE, ($°K \cdot sec$) | Interior diameter of helical tube (cm) | Length of temperature controlled capillary (cm) |
|---|---|---|---|---|
| 2.5 | 0.1 | 70 | 0.05 | 83 |
| | | 300 | 0.05 | 1502 |
| | 2.7 | 70 | 0.2 | 92 |
| | | 300 | 0.2 | 1511 |
| 8.0 | 0.1 | 70 | 0.11 | 79 |
| | | 300 | 0.11 | 1498 |
| | 2.7 | 70 | 0.44 | 84 |
| | | 300 | 0.44 | 1503 |

As a result of the inventive geometry of the cell conditioning device and sample-taking device, the optimal metabolite sample-taking occurs only in a narrow temperature range and in a time interval which is exactly determined thereby, wherewith the cell suspension is favorably influenced in that the cell metabolism is rapidly quenched and the intracellular metabolite is completely liberated, with retention of the cell structure. At all times during the process, the temperature is kept below the boiling point of the sample suspension.

Accordingly, in a preferred embodiment of the invention, in a cell conditioning device, for a "thermal equivalent" of 70-300° K.·sec which is to be transferred, advantageously a length of the temperature-controlled capillary segment of c. 80-1510 cm is chosen; and:
(a) For a low volumetric flow rate of c. 2.5 mL/sec:
i. at a lower conversion time ("turnover time") of the metabolite of
c. 0.1 sec, the interior diameter of the capillary is c. 0.5 mm;

ii. at an upper conversion time ("turnover time") of the metabolite of c. 2.7 sec, the interior diameter of the capillary is c. 2 mm;

(b) For a high volumetric flow rate of c. 8 mL/sec:
i. at a lower conversion time ("turnover time") of the metabolite of
c. 0.1 sec, the interior diameter of the capillary is c. 1 mm, particularly 1.1 mm;
ii. at an upper conversion time ("turnover time") of the metabolite of
c. 2.7 sec, the interior diameter of the capillary is c. 4 mm, particularly 4.4 mm.

By appropriate modification of the geometry of the inventive sample-taking system, it is possible to realize, e.g., a metabolomics analysis, particularly in an HD screening process.

The claimed matter of the invention further includes a cell conditioning device in the form of a sample-taking device for sampling from a source of the liquid culture medium containing the cell(s), which device is comprised of a sample transferring segment and a sample receiving unit.

The course of the temperature of the cell suspension in the inventive device is illustrated schematically in FIG. 2.

Temperature of the sample (abscissa) versus section of the sample-taking segment.

The following quantities are employed for the purpose of explanation of the inventive device:

T_heat-source: The temperature applied to the capillary by the heat source (corresponds to the conditioning temperature, $T_K$);

T_suspension: The temperature of the suspension in the culturing system (corresponds to the culturing temperature, $T_M$);

T_sample-taking vessel: The temperature of the metabolite solution in the sample-taking vessel;

s_dead: The section from the entrance into the sample-taking system to the start of the temperature-controlled capillary section in which temperature-controlled section temperature control is effected by the heat source;

s_hot: The section through which the sample is passed from the start of the temperature-controlled capillary section (acted on by the heat source) at the temperature of the suspension, until the sample reaches the temperature of the heat source;

s_holding: The section of the temperature-controlled capillary which the sample passes through at the temperature of the heat source;

s_heat-source: The length of the temperature-controlled capillary section in which temperature control is effected by the heat source (which section is the sum of the hot section and the holding section);

t_dead: The time period required for the sample to pass through the dead section;

t_hot: The time period required for the sample to pass through the hot section;

t_holding: The time required for the sample to pass through the holding section (corresponds to the conditioning time, $t_h$);

t_heat-source: The time required for the sample to pass through the heat source section.

If one draws the sample from the culturing system at a temperature of the suspension, preferably (and typically) 30-37° C. for microorganisms and cell cultures, the sample will first pass through a transfer section (the dead section), and when it enters the temperature-controlled capillary it is brought within a short section, the hot section, to exactly the temperature of the heat source, preferably ±5° C., wherewith subsequently, by being mixed with already present sample solution in the sample receiving vessel the said sample will be cooled to the temperature of the sample receiving vessel, preferably 4° C. In this connection, the length of the hot section s_hot, depends in particular on the properties of the cell suspension, the geometry of the overall sample-taking system, the flow-through time employed, and the temperature applied by the heat source. Because of the, preferably, short heating time, for the inventive use of the "thermal equivalent" the time required for the sample to pass through the hot section s_hot, namely the hot section time t_hot, is reckoned as part of the "holding section time" (t_holding) of holding at the temperature of the heat source. The holding section time t_holding is the time period required for an infinitesimally small volume element at the mean flow speed to pass through the temperature-controlled capillary segment s_holding.

FIG. 1 illustrates an exemplary embodiment of a cell conditioning device (sample-taking device) according to the invention. A source 1, particularly a bioreactor, has been charged with a preferably liquid culture medium 2 in which the biological cells of interest are disposed. Preferably the cells are in a culture suspension in the bioreactor. The device is further comprised of at least one capillary 3 which is disposed adjacent to a heat source 4. Preferably the heat source is thermally coupled to the capillary over a particular "hot section", such as to facilitate heat flow between the heat source and the lumen of the capillary. This "hot section" corresponds to the length of the temperature-controlled segment of the capillary.

Accordingly, the claimed matter of the invention further includes the use of the cell conditioning apparatus for recovery of a component material from a biological cell, wherewith in particular the herein described method is employed.

The claimed matter of the invention also includes the use of the cell conditioning device for quantitative determination of a component material in a biological cell, wherewith in particular the herein described method is employed.

Finally, the claimed matter of the invention further includes the use of the cell conditioning device for qualitative detection of a component material in a biological cell, wherewith in particular the herein described method is employed.

In the following the concepts of "ghosts", "ghost factor", "trues", "debris", and "debris factor" play important roles; accordingly, their definitions and methods of determination will now be presented.

In the context of the present invention the following definitions apply:

Ghost: A cell having an irreversibly damaged cytoplasmic membrane but which is nonetheless present in the form of an "empty" cell envelope;

True: A cell having an intact cytoplasmic membrane;

Debris: A fragment or fragments, of a cell which cell has suffered damage to its cellular integrity. A few of the many examples of debris which might be mentioned are: lipid micelles, individual proteins, mRNA, and naked or protein-bound DNA fragments;

Ghost factor: A quantitative equivalent from which the number of ghosts is determined;

Debris factor: A quantitative equivalent from which the number of debris pieces is determined.

The invention will now be described with reference to the accompanying Figures and examples, which (Figures and examples) should not be understood to limit the scope of the invention.

Figure 1:
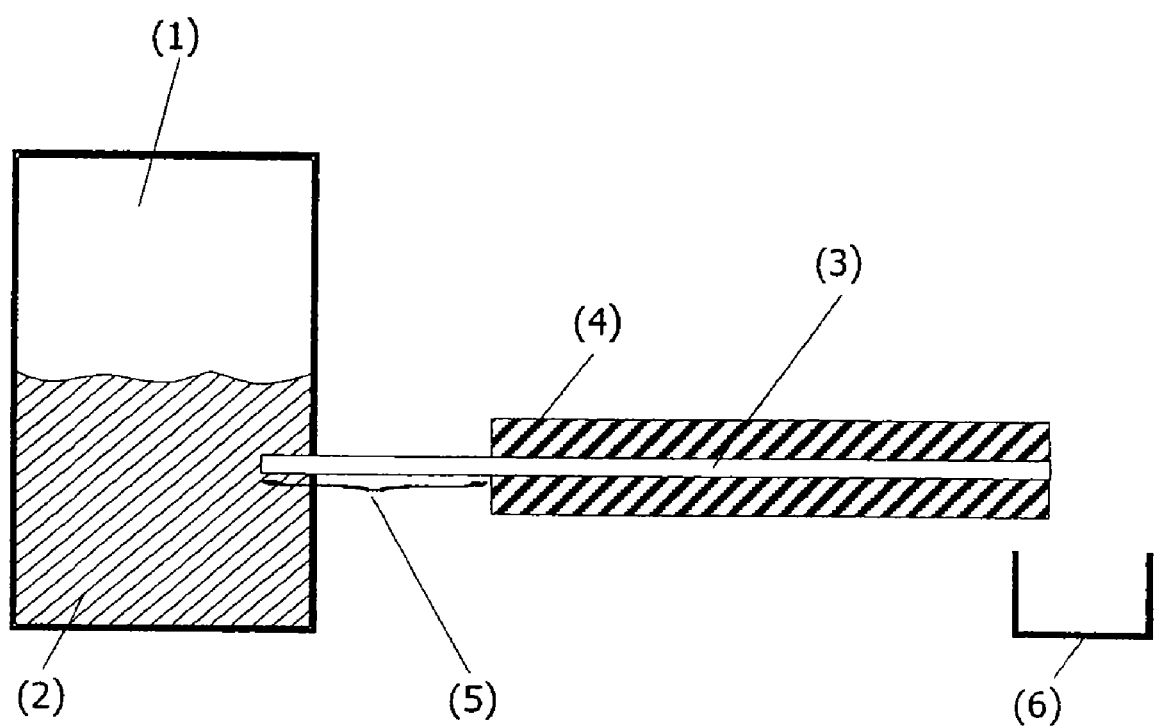
FIG. 1 is a simplified schematic of the inventive device.
Figure 2:
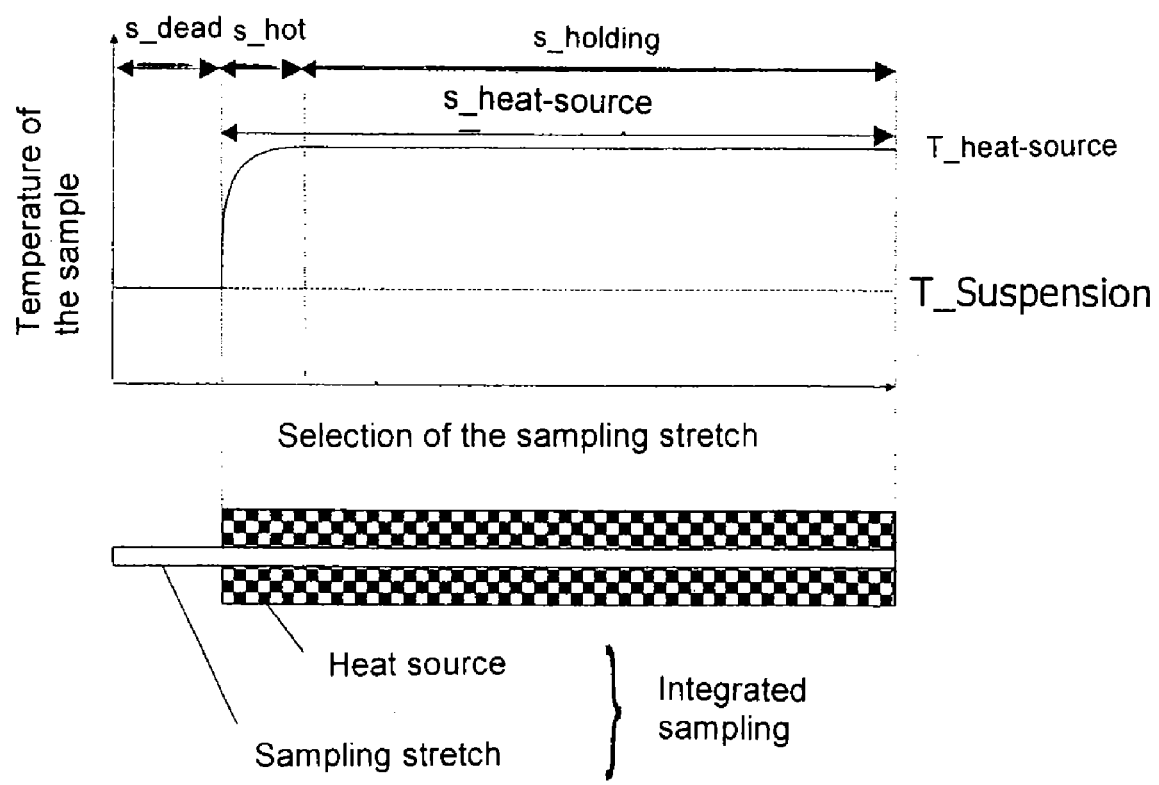
FIG. 2 is a schematic temperature profile in the inventive device.
Figure 3:
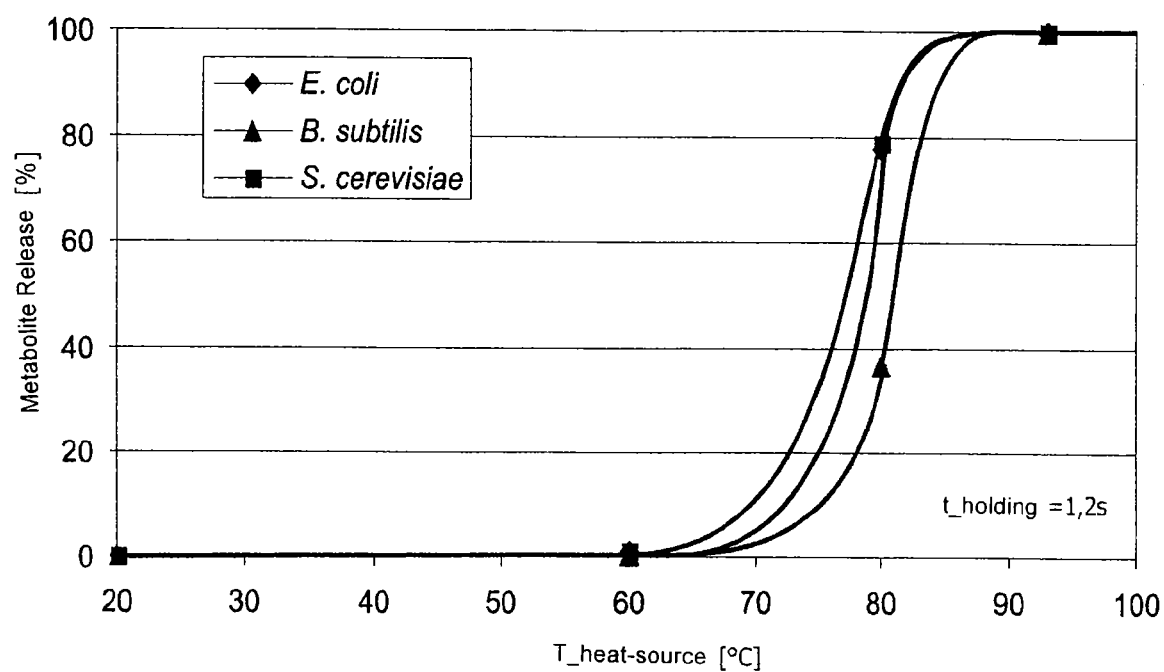
Figure 4:
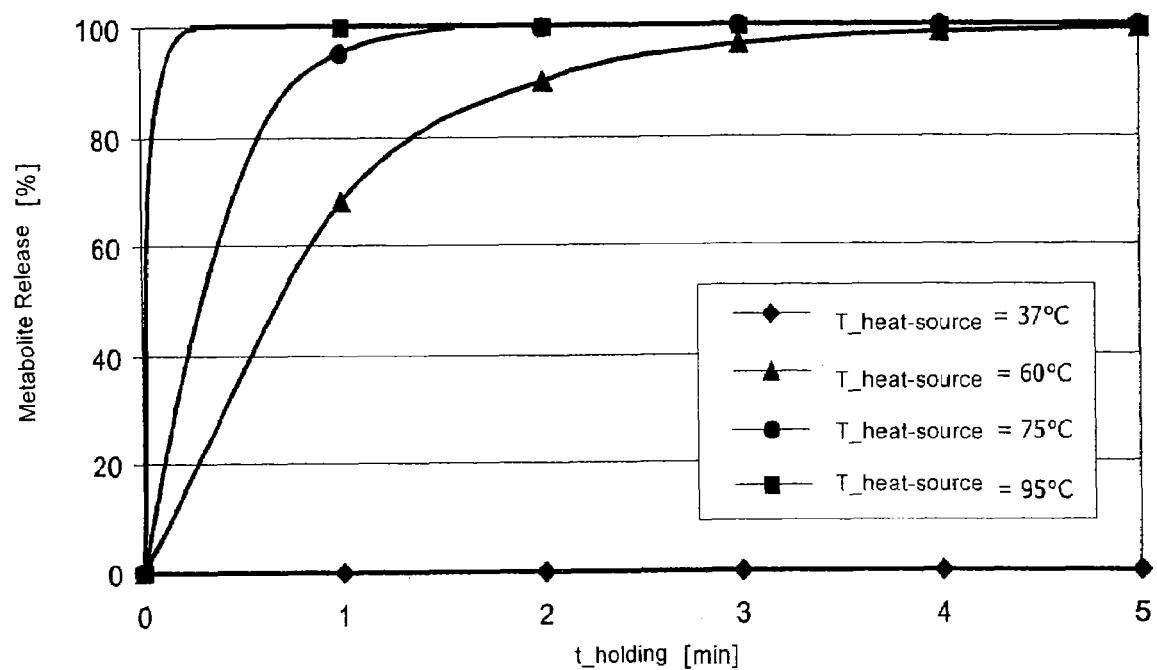
Figure 5:
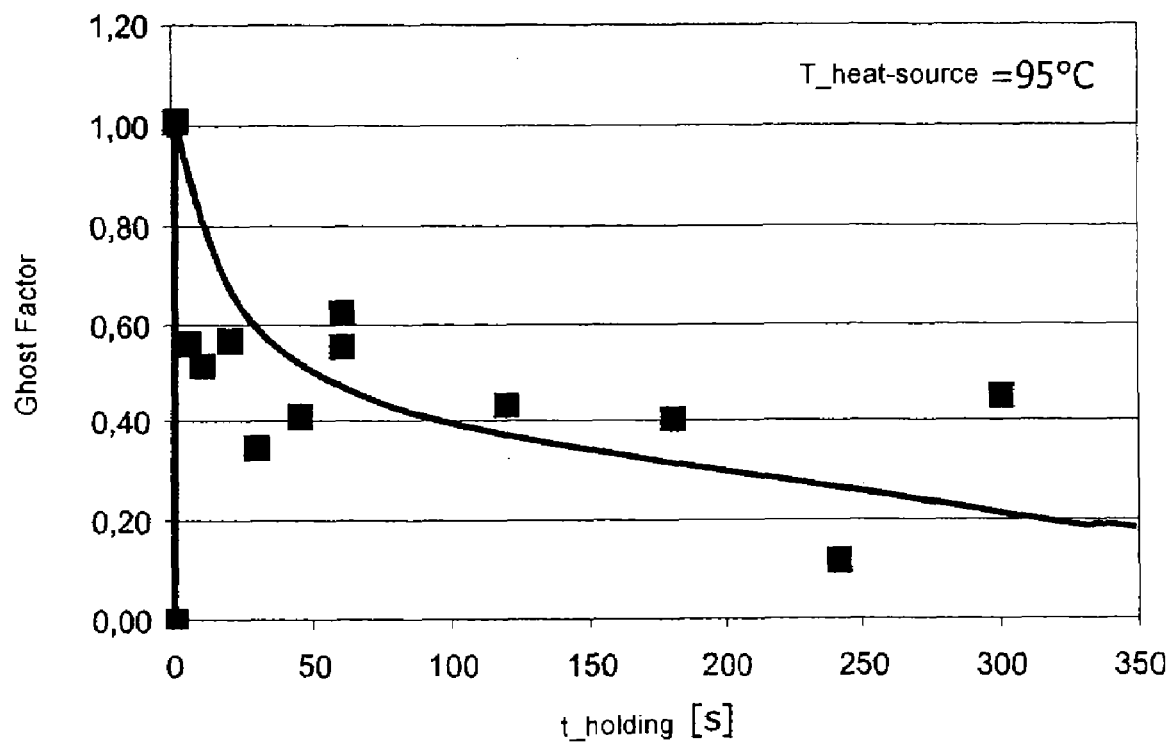
Figure 6:
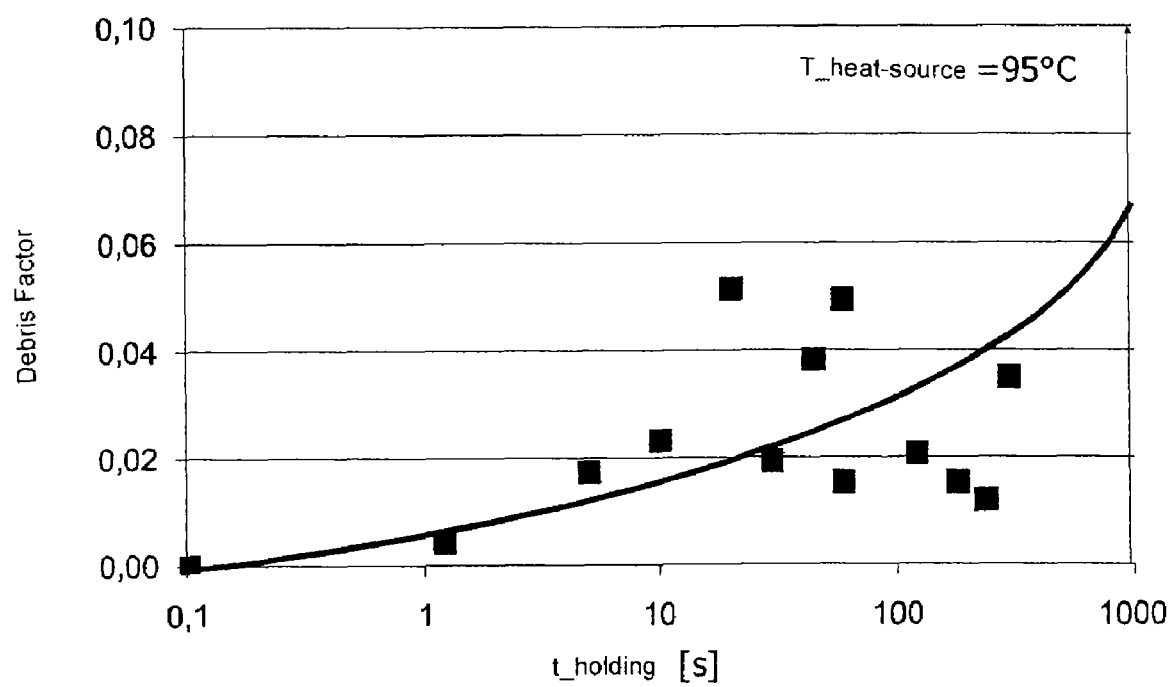
Figure 7:
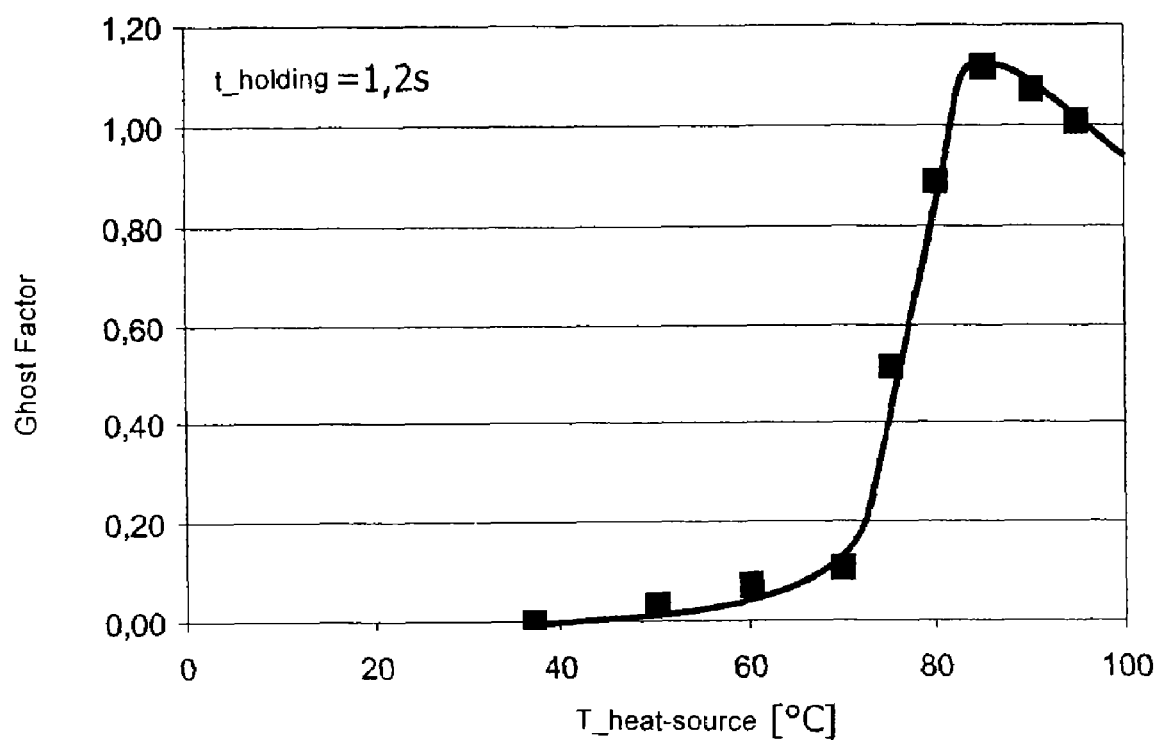
Figure 8:
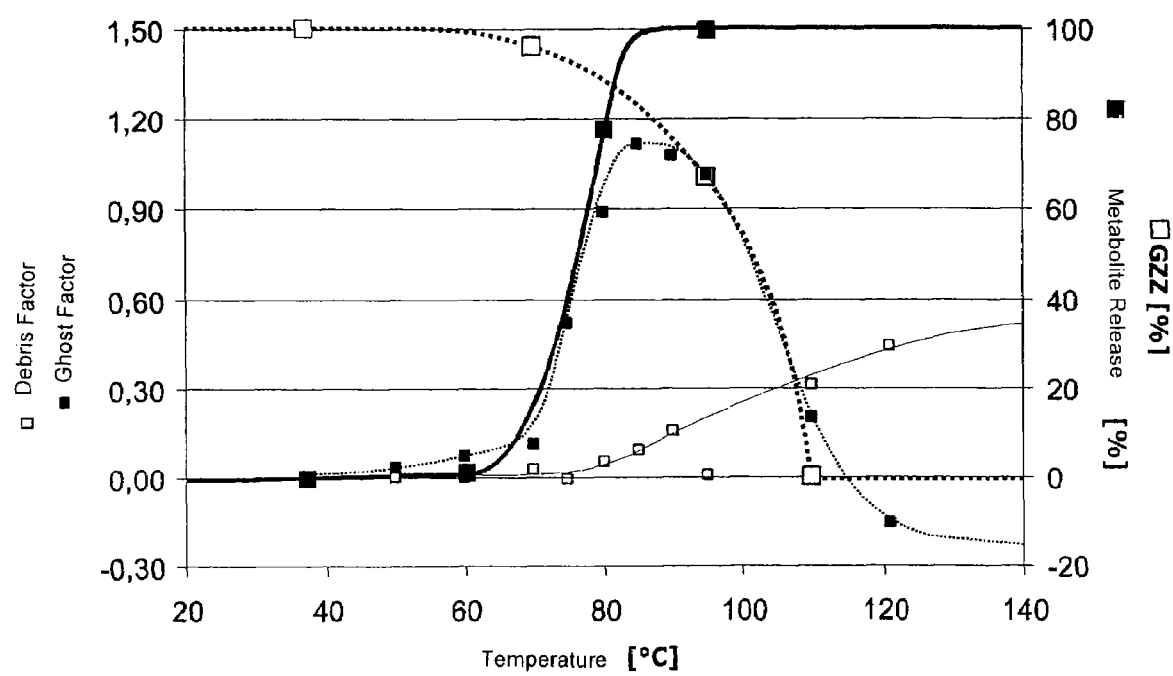
Figure 9:
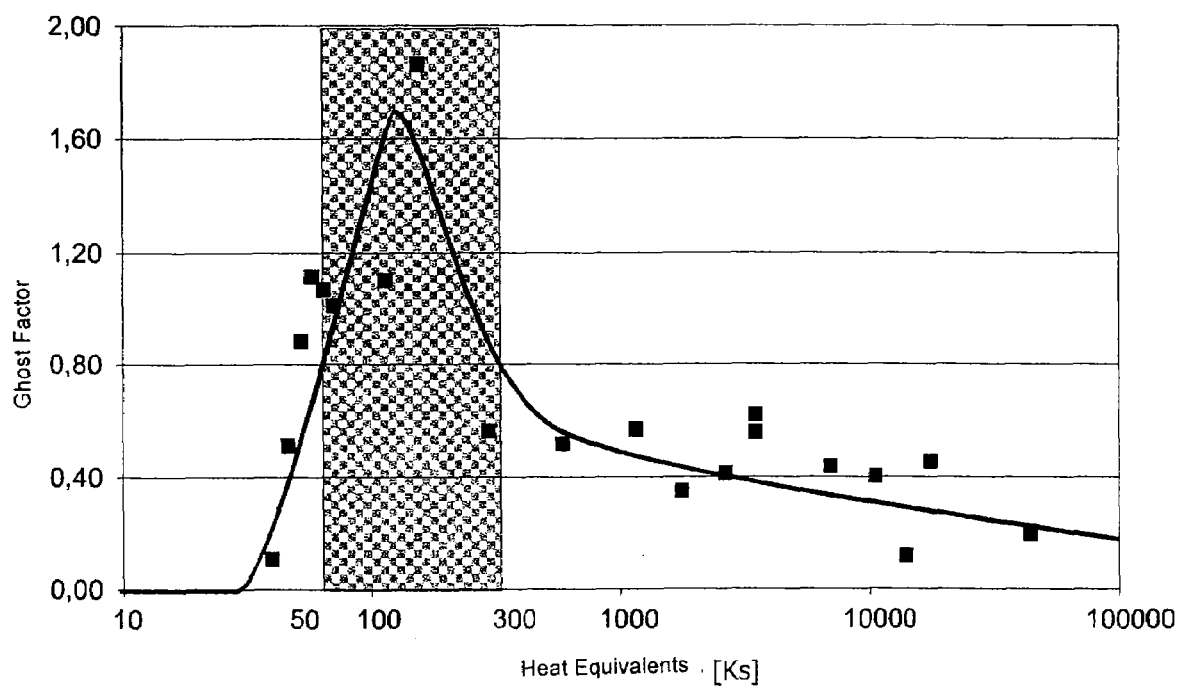
Figure 10:
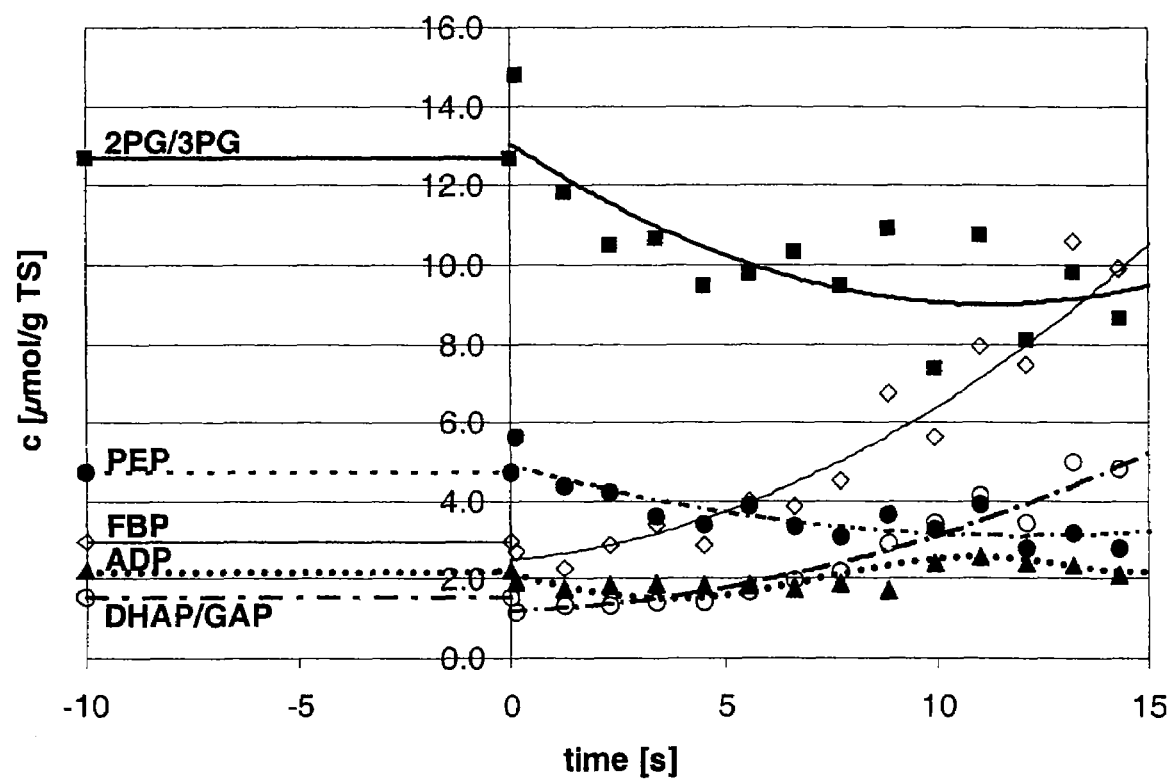

FIG. 3 is a plot of the degree of liberation of metabolites from the microorganisms *E. Coli, B. subtilis*, and *S. cerevisiae*, versus the applied temperature of the heat source, $T_K$. There is no appreciable liberation of metabolites at temperatures $\leq 60°$ C. Complete liberation is achieved at a conditioning temperature $T_K$ of c. 95° C. The conditioning time was 1.2 sec;

FIG. 4 is a plot of the degree of liberation of metabolites (%) versus the holding section time t_holding (minutes), for *E. coli*. Different conditioning times $t_h$ are required for complete liberation of metabolites, for different conditioning temperatures $T_K$. Accordingly, it is necessary that a threshold temperature, the critical temperature with respect to metabolites, T_krit, Metabolit, be exceeded;

FIG. 5 is a plot of the generation of ghosts at a conditioning temperature $T_K$ of 95° C. versus the conditioning time $t_h$ (seconds), for an *E. coli* culture;

FIG. 6 is a plot of the generation of cell debris in connection with the inventive device, at a conditioning temperature $T_K$ of 95° C. versus the conditioning time $t_h$ (seconds), for *E. coli*;

FIG. 7 is a plot of the generation of ghosts versus the conditioning temperature $T_K$, at a conditioning time $t_h$ of 1.2 sec, in sample-taking from an *E. coli* culture by means of the inventive device;

FIG. 8 is a plot of the surprising relationship between generation of cell debris, generation of ghosts, liberation of metabolites, and total number of cells (GZZ), all plotted versus the conditioning temperature $T_K$;

FIG. 9 is a plot of the generation of ghosts versus the "thermal equivalent" value, WE, employed. For *E. coli*, a truly satisfactory generation of an advantageously high number of ghosts occurs only for WE in the fairly narrow range of 70-300° K.·sec, with the optimum value of WE being 110° K.·sec;

FIG. 10 shows the results of analyses for metabolites which are in certain selected classes of substances, which metabolites have been liberated with sample taking and sample transferring according to the invention. Legend: PEP=phosphoenol-pyruvate; DHAP/GAP=sum of dihydroxyacetone phosphate and glyceraldehyde-3-phosphate; ADP=adenosine diphosphate; 2PG/3PG=sum of 2-phosphoglycerate and 3-phosphoglycerate; FBP=fructose diphosphate.

EXAMPLE 1

Liberation of Metabolites

The ability of the inventive apparatus, in the form of an integrated sample-taking system, to bring about liberation of metabolites was followed in an example of liberation of ATP. The ATP concentrations were determined with the aid of an enzymatic bioluminescence method (Tran and Unden, 1998, "Changes in the proton potential and the cellular energies of *Escherichia coli* during growth by aerobic and anaerobic respiration or by fermentation", *Eur. J. Biochem.*, 251, 538-543). As a rule, ATP from lysed cells, similarly to most metabolites, is expected to be present in only minimal amounts in cell suspension. Because of its ionic phosphate groups, ATP can diffuse in only extremely negligible amounts through the cytoplasmic membrane. The metabolite liberation tests were carried out with *E. coli* cultures as characteristic representatives of gram-negative prokaryotic cell suspensions, with *B. subtilis* cultures as characteristic representatives of gram-positive prokaryotic cell suspensions, and with *S. cerevisiae* cultures as characteristic representatives of eukaryotic cell suspensions. In the following presentation, "complete" liberation of the metabolite will be defined as determined of more than 95% of the ATP amount which can be determined from rapid quenching of the cell suspension with boiling water for 2 min followed by ultrasound degradation for 30 sec (using a Type UW 2200 ultrasound device supplied by Bandelin Electronic, 12207 Berlin, Germany).

1.1 Liberation of Metabolites: Dependence on the Conditioning Time, $t_h$:

For a given temperature of the heat source, corresponding to the conditioning temperature $T_K$, the holding section time t_holding (corresponding to the conditioning time $t_h$) plays an important role in the degree of metabolite liberation. In order to investigate the influence of the conditioning time $t_h$ on metabolite liberation, the conditioning time $t_h$ was varied for *E. coli* at various temperatures [$T_K$] (30° C., 60° C., and 95° C.). The results are presented in FIG. 4. At a conditioning temperature $T_K$=95° C., "complete" metabolite liberation was achieved with conditioning times $t_h$ substantially less than 1 min. At a conditioning temperature $T_K$=60° C., "complete" metabolite liberation was not achieved for conditioning times $t_h$ less than 5 min. At lower temperatures, "complete" metabolite liberation was not achieved within any acceptable time (not less than 5 min); and at a conditioning temperature $T_K$=37° C. there was no longer any observable increase in metabolite liberation. Thus the conditioning temperature $T_K$ applied by the heat source must exceed a threshold temperature T_krit,min in order for "complete" liberation of the intracellular metabolite(s) to be achievable in any practicable time (conditioning time $t_h$), in particular (preferably) less than 5 min 1.2 Liberation of Metabolites: Dependence on the Conditioning Temperature, $T_K$:

The dependence of the degree of metabolite liberation on the conditioning temperature $T_K$ at a given conditioning time $t_h$ (namely 1.2 sec) was determined, for cultures of *E. coli, B. subtilis*, and *S. cerevisiae*. The results are presented in FIG. 3. Whereas at conditioning temperatures $T_K$ below 60° C. no significant liberation of metabolites can be observed, at higher conditioning temperatures the degree of liberation rises significantly, and in all three cell systems "complete" liberation of the metabolite is achieved at temperatures of, at the highest, 95° C. Among the organisms tested, higher temperatures were required to attain comparable degrees of liberation of metabolites in the case of *B. subtilis* (chosen as an example of a gram-positive organism), compared to *S. cerevisiae* and *E. coli*.

EXAMPLE 2

Preservation of the "Structural Integrity"

Two important factors bearing on the preservation of the structural integrity of cells, in the context of the integrated sample-taking system, were identified, which factors are comparable to the metabolite liberation:

The conditioning time $t_h$, which corresponds to the holding section time t_halte when (preferably) the inventive apparatus is employed; and The applied conditioning temperature $T_K$, which corresponds to the temperature of the heat source associated with the capillary, T_heat-source, when (preferably) the inventive device is employed.

Advantageously, the determination of the "ghosts" is carried out with the use of the dye propidium iodide, which as a result of its positive charge can permeate only damaged membranes. Propidium iodide intercalates in the DNA and thereafter fluoresces in a red color, causing ghost cells to also fluoresce red. The ghosts in the present patent document were also determined quantitatively, with the aid of the "ghost factor".

The ghosts were determined quantitatively via the ghost factor. This quantity is obtained from the formula:

$$\text{Ghost factor} = ((red\_S-red\_C\_S)-(red\_Ref-red\_C\_Ref)) \div (green\_Ref-green\_C\_Ref),$$

where red_S is the red fluorescence of the treated sample suspension;

red_C_S is the red fluorescence of the treated, centrifuged sample suspension;

red_Ref is the red fluorescence of the untreated sample suspension;

red_C_Ref is the red fluorescence of the untreated, centrifuged sample suspension;

green_Ref is the green fluorescence of the untreated sample suspension; and green_C_Ref is the green fluorescence of the untreated, centrifuged sample suspension.

The red fluorescence was determined at 635 nm, and the green fluorescence at 535 nm, in microtitration plates with the aid of a microtitration plate measuring apparatus (Spectra Fluor type, provided by TECAN GmbH, of Crailsheim, Germany). The excitation was at 485 nm. In preparation of the measurement samples, the optical density of the sample suspension at wavelength 600 nm was determined, and the sample suspension was then diluted with 0.9% NaCl solution until an extinction of 0.06 at 600 nm was obtained. The sample suspension was then divided into 2 aliquots. One aliquot was stored over ice and was designated "sample suspension". The second aliquot was centrifuged 2 min at 14,000 rpm in a table centrifuge (type 5417R, supplied by Eppendorf AG, 22331 Hamburg, Germany), followed by collection of the supernatant. This aliquot was designated the "centrifuged sample suspension".

The further processing of the two aliquots was identical, as follows: 100 microliter of the aliquot was charged to the well of a microtitration plate, followed by 100 microliter of a dye mixture. The dye mixture was obtained from "Component A" of the L-7007 LIVE/DEAD® BacLight™ Bacterial Viability Kit (supplied by MoBiTec, of Göttingen, Germany), and contained 10 micromol/L SYTO® 9 and 10 micromol/L propidium iodide, in double distilled water. The designations "treated" and "untreated" refer to sample suspensions which were directly withdrawn from the culturing system (untreated), and sample suspensions which were processed by the integrated sample-taking system and/or were conditioned by alternative methods (treated).

The determination of the "trues" was carried out with the use of the dye SYTO® 9. This dye is un-charged and therefore can intercalate with DNA through intact membranes as well as damaged membranes. Therefore, when this dye is used alone it marks all cells: those with intact membranes ("trues") as well as those with damaged membrane ("ghosts"). When used in combination with propidium iodide, SYTO® 9 is reduced by propidium iodide and is driven out. Therefore only cells with intact membranes ("trues") will fluoresce green.

The "debris" was determined with the use of the "debris factor". This quantity is obtained from the formula:

$$\text{Debris factor} = ((red\_C\_S-red\_C\_Ref)/(red\_S-red\_C\_Ref) \times (red\_S-red\_Ref)/(green\_Ref-green\_C\_Ref)$$

where red_C_S is the red fluorescence of the treated, centrifuged cell suspension;

red_C_Ref is the red fluorescence of the untreated, centrifuged cell suspension;

red_S is the red fluorescence of the treated sample suspension;

red_Ref is the red fluorescence of the untreated sample suspension;

green_Ref is the green fluorescence of the untreated sample suspension; and green_C_Ref is the green fluorescence of the untreated, centrifuged sample suspension.

The method of determination of the "debris factor" was analogous to that for determination of the "ghost factor". The "debris factor" is a measurement of, principally, naked DNA fragments.

The total number of cells (GZZ) was determined with the aid of a counting chamber (supplied by Neubauer, and improved), under an optical microscope, and corresponds to the sum of the trues and ghosts.

2.1 Preservation of "Structural Integrity": Dependence on the Conditioning Time $t_h$:

In order to investigate the dependence of the "structural integrity" on the conditioning time $t_h$, various conditioning times $t_h$ were employed, at a conditioning temperature $T_K$ of 95° C. The results are presented in FIG. 5.

By definition, for the untreated cell suspension the ghost factor has a value of zero. For conditioning time $t_h$=1.2 sec, this surprisingly rose abruptly to 1.01. Beginning at conditioning times of 5 sec, and greater, it dropped rapidly to 0.56, gradually decreasing further with increasing [conditioning] times, as illustrated in FIG. 5. Thus it may be concluded that, surprisingly, in order to preserve the cellular integrity, not only is a short conditioning time $t_h$ possible but it is also necessary; for longer conditioning times and for temperatures $T_K$ above T_krit,min there is an undesirable appreciable drop in cellular integrity.

In contrast to other cell degradation methods for liberation of metabolites, e.g. rotary ball mills or ultrasound, the integrated sample-taking system gives rise to much less cell debris; the measurement values obtained are presented in Table 2. The cell debris generated depends on the temperature applied by the heat source, T_heat-source (for temperatures above the threshold temperature, T_krit,min), and increases with time (see FIG. 6).

Table 2 shows the "debris factor" for sample-taking and metabolite liberation after treatment of the cell suspension by means of: the integrated sample-taking system; rotary ball mill(s); and ultrasound.

Rotary ball mills and ultrasound devices severely damage cellular integrity, and generate a substantially greater amount of cellular debris than does the inventive method.

TABLE 2

Thermal conditioning
(according to the invention):

| Conditioning temperature, $T_K$ (° C.) | Conditioning time, $t_h$ (sec) | "Debris factor" |
|---|---|---|
| 95 | 1.2 | 0.00 |
| 95 | 20 | 0.05 |
| 95 | 45 | 0.04 |
| Rotary ball mill, 11 min (comparison) | | 0.72 |
| Ultrasound degradation, 30 sec (comparison) | | 0.99 |

2.2. Preservation of "Structural Integrity": Dependence on the Conditioning Temperature $T_K$:

In order to investigate the dependence of the structural integrity on the temperature, the effects of temperature variations on ghost generation were analyzed. (Ghosts are cells from which the metabolites have been liberated but which retain their "structural integrity".)

The results for a conditioning time $t_h$ of 1.2 sec are presented in FIG. 7. Whereas at temperatures $T_K$ up to 75° C. only slight increases of ghosts (expressed as the "ghost factor") were observed, ghosts increased abruptly at higher conditioning temperatures, and reached a maximum at $T_K$=c. 85° C. At conditioning temperatures of 90 and 95° C., slight decreases in the "ghost factor" may be seen (FIG. 7). In comparison to known methods of metabolite liberation (e.g. rotary ball mills, and ultrasound), the liberation of metabolites by means of the inventive method advantageously results in much more ghosts than the known methods (see Table 3).

Table 3 shows the "ghost factor" for sample-taking and metabolite liberation after treatment of the cell suspension by means of: the integrated sample-taking system; rotary ball mill(s); and ultrasound.

Rotary ball mills and ultrasound devices severely damage cellular integrity, and generate a substantially greater amount of cellular debris than does the inventive method. Meanwhile, the inventive method gives rise to a substantially greater amount of ghosts than does treatment of the cell suspension by rotary ball mills or ultrasound.

TABLE 3

Thermal conditioning
(according to the invention):

| Conditioning temperature, $T_K$ (° C.) | Conditioning time, $t_h$ (sec) | "Ghost factor" |
|---|---|---|
| 95 | 1.2 | 1.01 |
| 95 | 20 | 0.57 |
| 95 | 45 | 0.41 |
| Rotary ball mill, 11 min (comparison) | | −0.05 |
| Ultrasound degradation, 30 sec (comparison) | | −0.12 |

Since the total number of cells (GZZ) is the sum of the "trues" and "ghosts", the underlying model requires that: as soon as no more trues are present, the metabolite liberation should be complete; with a decreasing number of ghosts, the amount of debris should increase; and there is an upper limiting temperature, above which no ghosts are formed but cell debris fragments increase in number.

These relationships were studied experimentally with *E. coli*, using culturing temperatures $T_K$ in the range 50-121° C. At conditioning temperatures above 100° C., it was necessary to use sample-taking devices which were different from the preferred device according to the invention, namely it was necessary to use a device allowing application of an overpressure to continuously avoid boiling of the sample suspension. The conditioning time $t_h$ was varied in the range 1.2-600 sec.

In FIG. 8, the experimental results are presented in a combined graphic. "Complete" metabolite liberation occurs when all trues have been converted to ghosts or debris. It can be shown that, suprisingly, at certain conditioning temperatures $T_K$, critical thresholds are reached. The plot of the "ghost factor" (which is a parameter indicating the number of ghosts formed) surprisingly shows an optimum in the range of $T_K$ of 65-105° C., particularly 80-95° C.

EXAMPLE 3

Combinatorial Optimum: "Thermal Equivalents"

As mentioned hereinabove, the use of rotary ball mills or ultrasound for metabolite liberation in a non-selective cell degradation process results in a large amount of debris (see Tables 2 and 3). In contrast, using the inventive method one can significantly reduce the amount of debris, and can optimize the amount of ghosts while liberating the metabolites (Table 3). From the above-described studies it is seen that the parameter combination of conditioning time $t_h$ and conditioning temperature $T_K$ is of major significance for the degree of metabolite liberation and for the preservation of the "structural integrity" of the cells. The following simple multi-factor model can be derived from the studies.

(1) For conditioning temperature $T_K \leq$ T_krit,min:

If the conditioning temperature $T_K$ which is applied is less than a critical temperature T_krit,min, the thermal treatment gives rise to only a very slow liberation of metabolites and a very slow generation of ghosts (as indicated by a low "ghost factor").

(2) For T_krit,min<conditioning temperature $T_K \leq$ T_krit,max, and conditioning time $t_h \leq$ t_krit,min:

In this case, ghosts are generated, and correlatively metabolites are liberated.

However, since the conditioning time does not exceed the minimum critical holding time t_krit, min, the formation of ghosts is not maximal, and "complete" metabolite liberation does not occur.

(3) For T_krit,min<conditioning temperature $T_K \leq$ T_krit,max, and t_krit,min<conditioning time $t_h \leq$ t_krit,max:

Under this scenario, ghost formation is optimum, with "complete" liberation of metabolites.

(4) For T_krit,min<conditioning temperature $T_K \leq$ T_krit,max, and conditioning time $t_h$>t_krit,max:

Under this scenario, metabolite liberation is "complete", but, with the conditioning time exceeding the maximum critical holding section time, t_krit,max, the "structural integrity" of the cells is damaged, and the ghosts give rise to a significant amount of debris.

(5) For conditioning temperature $T_K$>T_krit,max:

Under this scenario, again metabolite liberation is "complete", but, with the conditioning temperature exceeding the critical maximum temperature T_krit,max, very few ghosts are produced. Therefore, poor results are obtained if one attempts to process the sample suspension.

Values obtained for the critical minimum and maximum applied temperatures in the capillary with temperature control from the heat source, T_krit,min and T_krit,max, are given in Table 4, for the cell systems employed, viz. *E. coli, B. subtilis,* and *S. cerevisiae*.

TABLE 4

| Example system | Minimum critical applied temperature, T_krit, min | Maximum critical applied temperature, T_krit, max |
|---|---|---|
| E. coli | 70° C. | Boiling point of the sample solution, viz. 105° C. |
| B. subtilis | 75° C. | Boiling point of the sample solution, viz. 105° C. |
| S. cerevisiae | 70° C. | Boiling point of the sample solution, viz. 105° C. |

The critical minimum and maximum holding section times, t_krit,min and t_krit,max, are not fixed quantities but depend on, in particular, the applied conditioning temperature. In order to arrive at an optimal combination of the parameters conditioning time $t_h$ and conditioning temperature $T_K$ for advantageous dimensioning of the inventive device, both parameters are combined by multiplication, and the product is designated the "thermal equivalent" (WE), having units of measure of ° K.-sec. Prior to the multiplication, the culturing temperature of the organism, $T_M$ (° K.), is subtracted from the applied conditioning temperature $T_K$ (° K.).

E.g., for E. coli the culturing temperature $T_M$ is 310° K., corresponding to c. 37° C. Accordingly, for E. coli the optimum value determined for WE was 110±20° K. (Table 5).

The optimum WE values (WE_opt) determined for other biological systems are also presented in Table 5.

TABLE 5

| Example system | | Minimum value of "thermal equivalent", WE_min | Optimum value of "thermal equivalent", WE_opt | Maximum value of "thermal equivalent", WE_max |
|---|---|---|---|---|
| E. coli | (example of a gram-negative prokaryote) | 70 | 110 | 300 |
| B. subtilis | (example of a gram-positive prokaryote) | 90 | 130 | 300 |
| S. cerevisiae | (example of a eukaryote) | 70 | 110 | 260 |

EXAMPLE 4

Geometry of the Integrated Sample-Taking System

The knowledge about the "thermal equivalent" WE as a function of the conditioning time $t_h$, conditioning temperature $T_K$, and culturing temperature $T_M$, leads to specification of geometric constraints and criteria for the geometric design. It is necessary to observe these constraints in order to achieve:

(i.) sufficiently rapid quantitative liberation of the metabolites (in the step of transferring through the dead volume and accomplishment of the quenching), in which connection the time constants of the biochemical reactions should be taken into account (the "turnover time"); and (ii.) cells having the desired structure, particularly "ghost cells", through the choice of characteristic conditioning times.

(iii.) A further constraint results from the requirements of the subsequent analysis of the sample, the minimum sample volume (reflected in the volumetric flow rate).

The geometric design must ensure that, for the quenching step, the determined critical temperature, T_krit, min<T_krit<T_krit,max, is reached in the heating section, s_hot, within the heating time t_hot.

The controlling factor here is the time t_hot needed for quenching of the metabolism.

Starting from a balance of the heat flows, the geometric relationships can be obtained:

$$\rho \cdot \dot{V} \cdot c_p \cdot (T_{Suspension} - T_{WT}) = \qquad \text{(Equation 1)}$$

$$-Nu \cdot \lambda \cdot \pi \cdot S_{hot} \cdot \frac{(T_{WT} - T_{Suspension}) - (T_{WT} - (T_{WT} - 5\ \text{K}))}{\ln\frac{(T_{WT} - T_{Suspension})}{(T_{WT} - (T_{WT} - 5\ \text{K}))}}$$

In our system, T_WT is equivalent to the applied temperature of the heat source, T_heat-source. Applying a suitable criterion relationship of the form $$Nu = c \times Re^m \times Pr^n,$$

for the Nusselt number (ref. VDI-Wärmeatlas [(in German)]), one obtains (Equation 2):

$$\rho \cdot \dot{V} \cdot c_p \cdot (T_{Suspension} - T_{heat-source}) =$$

$$-\left(3.953 + 0.0864 \cdot \left[1 + 0.8 \cdot \left(\frac{d}{D}\right)^{0.9}\right] \cdot \left(\frac{4 \cdot \dot{V}}{\pi \cdot d \cdot \nu}\right)^{0.652} \cdot 3.4^{1/3}\right) \cdot \lambda \cdot \pi \cdot S_{hot} \cdot 58\ \text{K}$$

Data concerning the materials (based on water at various temperatures) are presented below in particular the dimensionless Reynolds number Re and dimensionless Prandtl number Pr, for determination of fluid dynamics and heat transfer, are presented below; also the geometric parameters (d and D) of the sample-taking system employed:

| | |
|---|---|
| Re (=0.5 × (Re(35° C.) + Re(90° C.)) | 4900 |
| Pr (=0.5 × (Pr(35° C.) + Pr(90° C.)) | 3.4 |
| c/m/n, with m = m(d, D) | 0.083/0.652/0.333 |
| d | 2.03 mm |
| D | 57 mm |
| w | 1.08 m/sec |
| delta-Tm | 58° K |
| $\dot{Q}$ | 781 W. |

With the materials data based on an average of the values at different temperatures (rho (p)=0.979 mg/L, $c_p$=4.192 kJ/kg K, nu=0.525×10$^{-6}$ sq m/sec, lambda=0.652 W/m K, and, as technical constraints, a sample-taking frequency of f=5/sec (corresponding to a volumetric flow rate of at least 2.5 mL/sec), and a helix diameter of the helical tubing of 0.057 m (see Table 6 for materials data, dimensionless numbers for fluid dynamics calculations and heat transfer calculations, and the geometric parameters d and D), in particular the following equation follows for the geometric parameter s_hot:

$$S_{hot} = \frac{1}{0.618 + 0.02 \cdot \left[1 + 0.8 \cdot \left(\frac{d}{0.057}\right)^{0.9}\right] \cdot \left(\frac{6.06}{d}\right)^{0.5 + 0.2903 \cdot (d/0.057)^{0.194}}} \quad \text{(Equation 3)}$$

The number of "thermal equivalents" to be transferred in the integrated sample-taking system depends on the organisms used, i.e. the specific intracellular metabolite pool concentrations; and through suitable dimensioning, one should achieve the result that, in the time needed for the process of transport through the dead volume and the process of quenching, a maximum of 10% of this pool concentration can be converted in the sample-taking segment. Losing 10% of the pool concentration may be deemed acceptable, in a context of quantitative analysis. ATP was taken as an example, because it has high "turnover"; accordingly, the "turnovers" taken into account in the calculations were those for ATP. Intracellular ATP concentrations, specific ATP rates of formation, and turnover, tau, for the organisms taken into account are summarized in Table 6.

Table 6 gives the intracellular ATP concentration, specific ATP formation rates, and "turnover", tau, for the different cell systems. The cell system *E. coli* is representative of gram-negative prokaryotes, *B. subtilis* is representative of gram-positive prokaryotes, and *S. cerevisiae* is representative of single-cell eukaryote systems. Extreme values are tau(ATP)= 0.1 sec and 3 sec.

TABLE 6

| Cell system | cATP (concentration, micromole/g TS) | qATP, rate of formation, mmol/g TS/hour | tau(ATP), "turnover time", sec |
|---|---|---|---|
| Dilution time, D = 0.1/hour: | | | |
| *E. coli* | 0.7-7.6 | 13-25 | 0.1-2.1 |
| *B. subtilis* | 1.8 | 15.5 | 0.4 |
| *S. cerevisiae* | 0.4-8.0 | 10.8 | 0.1-2.7 |
| Dilution time, D = 0.4/hour: | | | |
| *E. coli* | 8.7 | 60.5 | 0.5 |
| *B. subtilis* | 1.8 | 55.2 | 0.1 |
| *S. cerevisiae* | 0.4-8.0 | 69.8 | c. 0.4 |

Accordingly, the following relationship holds:

$$d = \left(\frac{4 \cdot \dot{V} \cdot \frac{0.1 \cdot c_{ATP}}{q_{turnover(ATP)}}}{\pi \cdot S_{hot}}\right)^{0.5} \quad \text{(Equation 4)}$$

where: $q_{turnover(ATP)}$ is the "turnover" rate of ATP;
s_heat is the length of the heating section.

The solution of the heat balance according to Equation 1 provides the length of the heating section, s_heat, of the quenching process, which length is needed for "transfer of the thermal equivalents". This depends on the inner diameter of the helical tubing, in Equations 3 and 4.

If the critical temperature, T_krit,min<T_krit<T_krit,max, is reached, the "thermal equivalents" must be transferred in the holding segment of the sample-taking apparatus, s_holding (FIG. 9).

The time, t_holding, is geometry-dependent, and is given by the following equation:

$$t_{holding} = \frac{\frac{WE_{opt}}{T_{heat\text{-}source} - T_{Suspension}}}{\dot{V}} - \frac{\pi \cdot d^2}{\left(2.472 + 0.08 \cdot \left[1 + 0.8 \cdot \left(\frac{d}{0.057}\right)^{0.9}\right] \cdot \left(\frac{6.06}{d}\right)^{0.5 + 0.2903 \cdot (d/0.057)^{0.194}}\right)} \quad \text{(Equation 5)}$$

where WE="thermal equivalents"; and opt=optimal.

The following equation gives the holding section length, s_holding:

$$s\_holding = t\_holding \cdot w \quad \text{(Equation 6)}$$

Accordingly, the length of the entire temperature-controlled segment, s_heat-source, is given by:

$$s\_heat\text{-}source = s\_hot + s\_cold. \quad \text{(Equation 7)}$$

(Length of the temperature-controlled segment=heating section length plus holding section length.)

In a preferred device configuration, the device is in the form of a tubular helix with the following characteristic geometric dimensions:

| | |
|---|---|
| Interior diameter of tubular helix: | d_i = 2.8-2.27/+1.7 mm |
| Heating section length: | s_hot = 16 ± 6 cm |
| Characteristic geometric parameter: | d_i/s_hot = 0.0175 ± 0.0135 |
| Length of the temperature-controlled capillary segment: | s_heat-source = 240-160/+1271 cm |

The deviations of the individual geometric parameters from the stated optimal value may result from the given cell system and culturing conditions, the specific "turnover" times (see Table 6), and the volumetric flow rate (which is preferably in the range 2.5-8.0 mL/sec). For small values of the interior diameter, d_i, less than 1.2 mm, by application of Equation 3 the helix diameter of the tubular helix should preferably be kept small (see the reference, VDI-Wärmeatlas).

List of Symbols

| Symbol | Designation | Units |
|---|---|---|
| $\dot{V}$ | Volumetric flow rate, through the integrated sample-taking: | cu m/sec |
| f | Sampling frequency | 1/sec |
| tau (τ) | Turnover: | sec |
| rho (ρ) | Density | kg/cu m |
| w | Mean flow speed | m/sec |
| d_i | Interior diameter of the tubular helix: | m |
| D | Helix diameter of the helix | m |

-continued

| Symbol | Designation | Units |
|---|---|---|
| delta-Tm | Mean logarithmic temperature difference: | K |
| Re | Reynolds number | (dimensionless) |
| Pr | Prandtl number | (dimensionless) |
| Nu | Nusselt number | (dimensionless) |
| c, m, n | (Certain coefficients and exponents.) | —. |
| $c_p$ | Heat capacity | kJ/(kg K). |
| nu(ν) | (Greek letter.) Kinematic viscosity | sq m/sec. |
| eta(η) | Dynamic viscosity | kg/(m sec). |
| lambda(λ) | Heat transfer coefficient | W/(m K). |

EXAMPLE 5

Recovery and Analysis of Intracellular Metabolites

The *E. coli* strain K-12 was cultured under sterile conditions in a bioreactor (KLF 2000, supplied by Bioengineering, of Wald, Switzerland), at a culturing temperature $T_M$ of 37° C. (c. 310° K.) (corresponds to T_suspension). Using the inventive integrated sample-taking apparatus, and implementing the following parameters, the sample was conditioned:

| | |
|---|---|
| Volumetric flow rate | 3.5 mL/sec |
| Capillary interior diameter d_i | 2.03 mm |
| Length of the temperature-controlled capillary segment, s_heat-source: | 205 cm |
| Conditioning temperature $T_K$ (and temperature of the heat source): | 95° C. |

At a conditioning temperature $T_K$ of 95° C. and a conditioning time $t_h$ of 1.9 sec, according to the invention a "thermal equivalent" WE of 110° K.·sec was transferred.

Result I:

During the course of the sample taking, it was possible to simultaneously quench the cell suspension and selectively degrade said suspension.

The analysis of the metabolites liberated from the conditioned cells was performed by ion chromatography (Dionex DX500) and LC-MS (Thermo Quest Finnigan AQA), following a simple filtration step with pore diameter 0.2 micron wherein the cell envelopes (ghosts) and any intact cells ("reals") were retained.

In repeated sample takings according to the invention, the timewise course of the concentrations of selected intracellular metabolites in a steady-state *E. coli* culture at D=0.1/hr, with concentration of the biomass of c=2.30 g/L (dry weight basis) in the bioreactor were observed, after at time t=0 sec an extracellular "impulse" of 0.3 g/L glucose had been added to the bioreactor. For purposes of example, measurements were made of phospho-enol-pyruvate (PEP), sum of dihydroxyacetone phosphate and glyceraldehyde-3-phosphate (DHAP+GAP), adenosine diphosphate (ADP), sum of 2-phosphoglycerate and 3-phosphoglycerate (2PG+3PG), and fructose biphosphate (FBP).

Result II:

FIG. 10 shows the results of analysis of certain metabolites in selected substance classes, which metabolites were liberated inventively during sample-taking and transfer.

What is claimed is:

1. A method for thermally liberating an intracellular metabolite from a biological cell, comprising:
    (a) culturing the cell in a culture medium at a culturing temperature $T_M$(° C.); and
    (b) then conditioning the cell at a conditioning temperature $T_K$(° C.) for a conditioning time $t_h$ (sec);
    wherein $T_K$, $T_M$, and $t_h$ are related by the formula $$t_h \cdot (T_K - T_M) = WE$$

wherein WE represents a "thermal equivalent" (K·sec), and is in the range 90-150 K·sec, and
    wherein the conditioning temperature $T_K$ is 80-95° C.

2. A method according to claim 1, wherein the conditioning temperature $T_K$ is always below the boiling point of the culture medium.

3. A method according to claim 1, wherein the conditioning time $t_h$ is 1.3-600 sec.

4. A method according to claim 1, wherein the culturing temperature $T_M$ is 26-42° C.

5. A method according to claim 1, wherein the biological cell is a gram-negative prokaryote or a eukaryote, and the thermal equivalent WE is 110±20 K·sec.

6. A method according to claim 1, wherein the biological cell is a gram-positive prokaryote, and the thermal equivalent WE is 130±20 K·sec.

7. A method according to claim 1,
    wherein the culture medium is a liquid, which liquid medium containing the biological cell is flowed into a capillary for conditioning and,
    wherein the conditioning occurs while the cell is disposed in a temperature-controlled segment of the capillary at the conditioning temperature, $T_K$, for the conditioning time, $t_{kh}$.

8. A method according to claim 7, wherein the culture medium is flowed into the temperature-controlled segment of the capillary at a volumetric flow rate of 0.5-12 mL/sec.

9. A method according to claim 1, wherein the culturing takes place in a culturing vessel, and the thermal conditioning takes place in a receiving vessel, into which the culture medium containing the biological cell has been transferred.

10. The method of claim 1, whereby the metabolite is liberated from the biological cell, further comprising:
    (c) isolating the liberated metabolite from the culture medium.

11. The method of claim 1, whereby the metabolite is liberated from the biological cell, further comprising:
    (c) quantitatively determining the amount of liberated metabolite in the culture medium.

12. The method of claim 1, whereby the metabolite is liberated from the biological cell, further comprising:
    (c) qualitatively detecting the liberated component material in the culture medium.

13. A method according to claim 1, wherein the intracellular metabolite is selected from the group consisting of amino acids and their derivatives, amines and their derivatives, carboxylic acids, alcohols, aldehydes, ketones, phosphate esters other than nucleic acids, nucleic acids and congeners, sugars and congeners, lipids, steroids, fatty acids, vitamins, coenzymes, and inorganic ions.

14. The method of claim 1, wherein $T_M$ is 30-38° C.

15. The method of claim 1, wherein $t_h$ is 1.3-180 sec.

16. The method according to claim 9, wherein the receiving vessel is a sample collection vessel.

* * * * *

UNITED STATES PATENT AND TRADEMARK OFFICE
CERTIFICATE OF CORRECTION

PATENT NO. : 7,585,617 B2  Page 1 of 1
APPLICATION NO. : 10/598377
DATED : September 8, 2009
INVENTOR(S) : Michael Dauner and Jochen Schaub It is certified that error appears in the above-identified patent and that said Letters Patent is hereby corrected as shown below:

Column 26, line 34, claim 7, delete "$t_{kh}$" and insert therefor -- $t_h$ --

Signed and Sealed this

Twenty-fourth Day of November, 2009

David J. Kappos
*Director of the United States Patent and Trademark Office*